United States Patent [19]

Leon et al.

[11] Patent Number: 5,365,934
[45] Date of Patent: * Nov. 22, 1994

[54] APPARATUS AND METHOD FOR MEASURING HEART RATE

[75] Inventors: Tomas Leon, Chicago; Teng Y. E. Hong, Naperville; Emil S. Golen, Barrington, all of Ill.; Donald J. Alexander, Milwaukee, Wis.

[73] Assignee: Life Fitness, Franklin Park, Ill.

[ * ] Notice: The portion of the term of this patent subsequent to Sep. 14, 2010 has been disclaimed.

[21] Appl. No.: 53,511

[22] Filed: Apr. 26, 1993

Related U.S. Application Data

[63] Continuation-in-part of Ser. No. 722,800, Jun. 28, 1991, Pat. No. 5,243,993.

[51] Int. Cl.⁵ .......................................... A61B 5/0402
[52] U.S. Cl. ..................................... 128/707; 128/704; 128/706; 128/708
[58] Field of Search ............... 128/695, 696, 698, 700, 128/702, 703, 706, 704, 708, 715, 713, 666, 661.07

[56] References Cited

U.S. PATENT DOCUMENTS 4,239,048 12/1980 Steuer ................................. 128/666
5,088,497 2/1992 Ikeda .............................. 128/661.07
5,109,863 5/1992 Semmlow et al. ................... 128/715

OTHER PUBLICATIONS

Applications Handbook, vols. 1, 2, 3 and 4.

Primary Examiner—George Manuel
Attorney, Agent, or Firm—Michael B. McMurry

[57] ABSTRACT

An exercise apparatus for measuring heart rate is provided which comprises a sensor for generating a signal which includes the biopotential signal produced by a heart. This signal is filtered, amplified and digitized. A computer autocorrelates the digitized signal. A plurality of signal indication routines then scan the autocorrelated output for the presence of periodic signals. Each of the signal indication routines uses different search or filter criteria, such as peak and wave form detection, and generates one (and in some cases, several) candidate heart rates. An arbitrator then selects one of the candidate heart rates according to predetermined criteria. These criteria include the value of previously selected heart rates. In one embodiment, the signal indication and arbitration routines are especially well-suited for measuring the heart rate of a user while exercising on a stair climbing machine or treadmill.

18 Claims, 14 Drawing Sheets

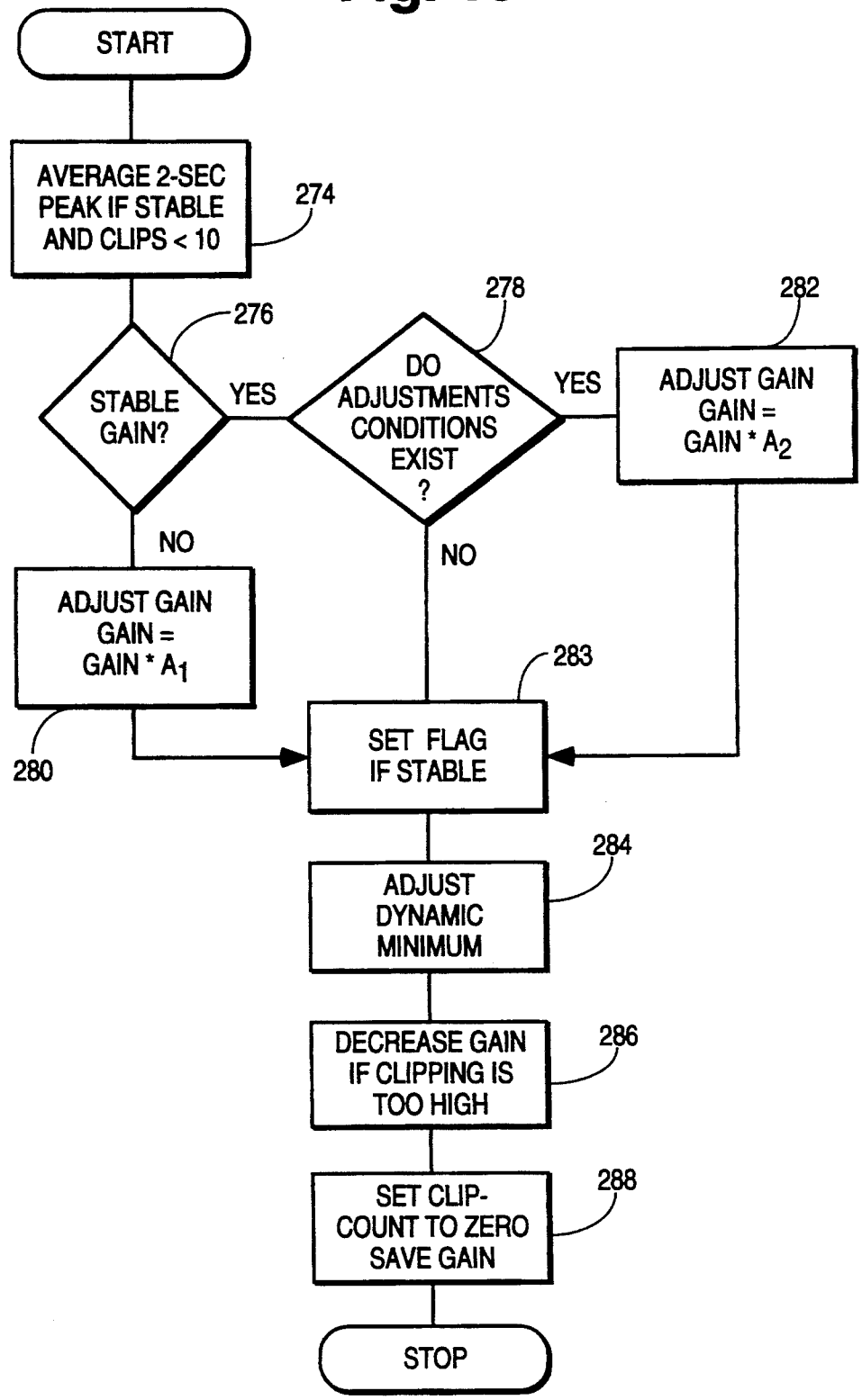

APPARATUS AND METHOD FOR MEASURING HEART RATE

RELATED APPLICATION

This Application is a continuation-in-part of U.S. patent application Ser. No. 07/722,800, filed on Jun. 28, 1991 now U.S. Pat. No. 5,243,993 and entitled "Apparatus and Method for Measuring Heart Rate," the disclosure of which is hereby incorporated by reference in its entirety.

FIELD OF THE INVENTION

The invention relates to the field of heart rate monitors, and in particular, to heart rate monitors used for measuring the heart rate of a person engaged in physical exercise.

BACKGROUND OF THE INVENTION

When the heart or other muscle contracts, the body generates a very low amplitude electric signal known as a biopotential signal. It is well known that this biopotential signal can be electronically detected on the surface of a person's skin. Because the heart expands and contracts in a regular rhythm, it generates a periodic biopotential signal. Thus, certain periodic voltage fluctuations on a person's skin correspond to heartbeat.

Devices for monitoring the heart rate of a human or animal are well known. Examples of these types of devices are described in U.S. Pat. Nos. 4,248,244; 4,540,001; and 4,898,182. Generally, most heart rate monitors use electrodes to sense voltage fluctuations on a person's skin. The signal thus sensed is then amplified and passed through a suitable filter for filtering out the biopotential signals unrelated to heart rate. The frequency of the residual signal is then determined and displayed as heart rate (in beats per minute).

Autocorrelation has been used to isolate heart rate from noisy biopotential signals in certain ideal conditions, such as found in hospitals. See U.S. Pat. No. 4,403,184. However, noise, particularly periodic noise, reduces the reliability of autocorrelation. This problem is particularly acute during physical exercise. Especially troublesome are repetitive exercises, such as performed on an exercise bike, stair climbing machine or treadmill. In repetitive exercises, muscles tend to be exerted in a rhythmic or periodic fashion, thereby generating a periodic biopotential signal which cannot easily be distinguished from heart rate. Moreover, because heart rate tends to vary during exercise, the steady rhythm of repetitive exercise motion may generate a stronger autocorrelated signal than actual heart rate.

Also problem prone is the interface between the human subject and the electrodes which are used to detect biopotential signals. In practice, persons exercising prefer to not be encumbered by the type of bracelet, harness or clip which is typically used to make contact between a person and the electrodes. Ideally, the electrodes are placed on a handlebar or other location which the person touches as a matter of course while exercising. Under these conditions, however, the person is likely to remove his or her hands from time to time, thereby complicating efforts to accurately and continuously monitor heart rate.

SUMMARY OF THE INVENTION

It is therefore an object of the present invention to provide an exercise apparatus for measuring heart rate having an autocorrelator. The apparatus has a sensor which generates an input signal that includes the biopotential signal produced by a heart. The autocorrelator periodically generates an autocorrelation signal of the input signal over a predetermined time period. Signal indication logic is responsive to the autocorrelation and detects the presence of a periodic signal in the autocorrelation signal. The signal indication logic then generates a heart rate signal corresponding to the frequency of the periodic signal.

In one embodiment of the invention, the signal indication logic includes logic for detecting a peak in the autocorrelation signal which is in excess of a first threshold value, and a peak which is in excess of a second threshold value. In another embodiment, the signal indication logic includes logic for detecting a pulse in the autocorrelation signal which has a waveform characteristic of a heartbeat. In some cases, the autocorrelator generates the autocorrelation signal in the time domain.

It is another object of the invention to provide an apparatus for measuring heart rate having an arbitrator which selects a heart rate signal from a plurality of candidate output signals according to predetermined criteria. The apparatus includes a sensor which generates an input signal that includes the biopotential signal produced by a heart. The apparatus also includes signal processing means responsive to the input signal which detect the indication of periodic signals in the input signal. The signal processor generates a plurality of output signals corresponding to each of the frequencies of these periodic signals. These output signals are the candidate output signals from which the arbitrator selects the heart rate signal.

In one embodiment the signal processor includes logic for detecting a peak in the input signal which is in excess of a first threshold value, and detecting a peak in the input signal which is in excess of a second threshold value. In another embodiment, signal processor includes logic for detecting a pulse in the input signal which has a waveform characteristic of a heartbeat.

In yet another embodiment, the criteria used by the arbitrator include reasonableness criteria. In one case, the arbitrator includes memory for storing the value of the selected candidate output signal, and the reasonableness criteria include rejecting a candidate output signal if its value deviates from the previously selected candidate output signal by more than a predetermined amount. In another case, the arbitrator includes a device which measures the rate of work being performed by the subject whose heart rate is measured, and the reasonableness criteria include rejecting a candidate output signal if its value is not proportional to the rate of work being performed by the subject. In yet another case, the reasonableness criteria including rejecting the candidate output signal if its value falls outside of a predetermined range.

It is another object of the invention to provide apparatus for measuring heart rate of a human while exercising, having an autocorrelator and an arbitrator. The apparatus has a sensor which generates an input signal that includes the biopotential signal produced by a heart. The autocorrelator is responsive to the input signal for periodically generating an autocorrelation signal of the input signal over a predetermined time period. The apparatus also has a signal processor which is responsive to the autocorrelation signal for detecting the indication of periodic signals therein. The signal processor generates a plurality of output signals corresponding to the frequency of these periodic signals. The arbitrator is responsive to these output signals, and selects that one of the output signals which most likely represents true heart rate, according to predetermined criteria.

In one embodiment, the apparatus also has an analog-to-digital converter which generates a digital signal corresponding to the input signal. In some cases, the autocorrelator is a programmable digital signal processor. In other cases, the apparatus includes a low pass digital filter which filters the signal between the analog-to-digital converter and the autocorrelator.

In another embodiment, the apparatus has an adjustable gain amplifier which amplifies the input signal, and logic which adjusts the gain of the adjustable gain amplifier so that its output remains within a predetermined range.

In yet another embodiment, the signal processor includes logic for detecting a pulse in the autocorrelation signal which has a waveform characteristic of a heartbeat. In some cases, the digital signal processor also includes logic for detecting a peak in the autocorrelation signal which is in excess of the first threshold value, and a peak which is in excess of a second threshold value. In some cases, the digital signal processor is a programmable digital signal processor.

In another embodiment, the sensor also has a plurality of electrodes which sense the biopotential signal produced by the human's body when the electrodes are placed into contact with the human. In some cases, the sensor also has a circuit responsive to the electrodes which generates a hands on/off signal that indicates whether the electrodes are in contact with the human. In other cases, the autocorrelator discontinues processing the input signal if the hands on/off signal remains at zero for a predetermined amount of time. The autocorrelator does not continue processing the input signal again until the hands on/off signal resumes a value other than zero.

In another embodiment of the invention, the arbitrator's predetermined criteria include reasonableness criteria. In some cases the apparatus further comprises circuitry for generating a motion signal corresponding to the frequency of repetitive motions performed by the human while exercising. In these cases, the reasonableness criteria include rejecting an output signal whose value is a multiple of the value of the motion signal.

BRIEF DESCRIPTION OF THE DRAWINGS

FIG. 19 is a logic flow chart illustrating the gain control operation of the digital signal processor of the apparatus shown in FIG. 2.

DETAILED DESCRIPTION OF THE INVENTION

1. Overview

Figure 1:
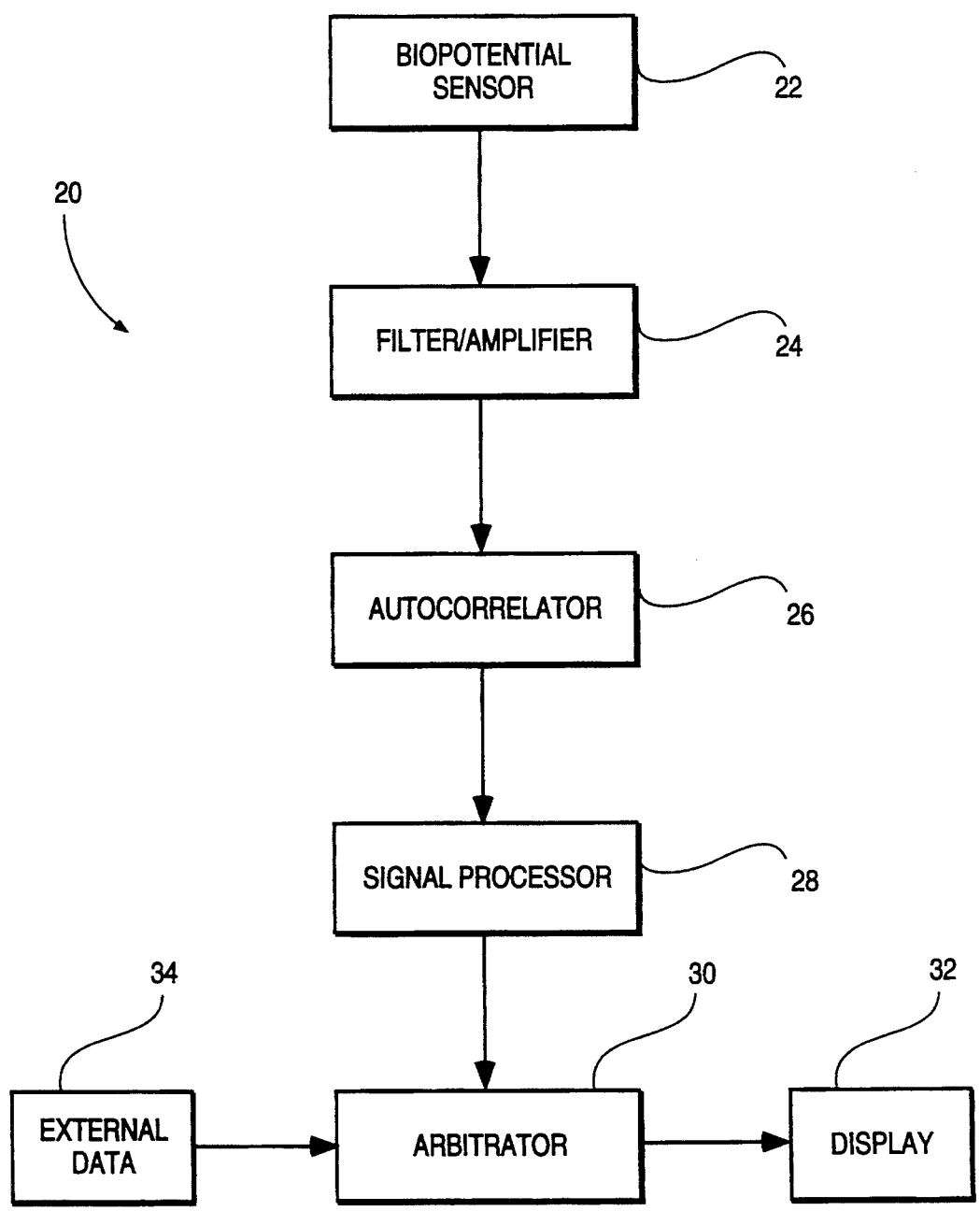
FIG. 1 is a block diagram of a generalized apparatus for measuring heart rate in accordance with the invention.

FIG. 1 is a block diagram of an apparatus 20 for measuring heart rate in accordance with the invention. Apparatus 20 comprises a biopotential sensor 22, a filter/amplifier stage 24, an autocorrelator 26, a signal processor 28 and an arbitrator 30. When the biopotential sensor 22 is placed in contact with a human subject, it generates an electric signal corresponding to the biopotential signals generated by the human. Generally speaking, the human body produces these biopotential signals when muscles, including the heart, expand and contract. Thus, the electric signal generated by the biopotential sensor 22 includes biopotential signals corresponding to the beating of the subject's heart. The electric signal also includes noise and signals corresponding to other bodily functions. As described in greater detail below, the primary function of apparatus 20 is to determine heart rate from the noisy signal comprising all of the subject's biopotential signals.

The output of the biopotential sensor 22 is applied to the filter/amplifier 24, where it is filtered and amplified after which the output of the filter/amplifier 24 is fed into the autocorrelator 26, which generates a signal that represents autocorrelation of the output of the filter-/amplifier 24. Autocorrelation algorithms are described in *Practical Approaches To Speech Coding*, Panos E. Papamichalis, Prentice-Hall, Inc., Englewood Cliffs, N.J., 1987. The output of the autocorrelator 26 is used as an input to the signal processor 28 which detects the presence of periodic signals in the output of the autocorrelator 26. The signal processor 28 generates a number of candidate signals, each of which corresponds to heart rate measured in beats per minute ("BPM"). To generate these signals, signal processor 28 employs several signal indicators for detecting the presence of a signal that could correspond to a heartbeat contained in the output of the autocorrelator 26. Each of these signal indicators (not shown in FIG. 1) employs a different technique, and generates one or more of the candidate signals.

The candidate signals are applied to the arbitrator 30, which uses predetermined criteria to decide which one of the candidate signals is most likely the subject's true heart rate. The heart rate selected by arbitrator 30 is displayed on display unit 32. The arbitrator 30 may take external data into account when selecting a heart rate. External data is supplied to the arbitrator 30 by an external data interface unit 34. The exact nature of the interface unit 34 depends on the environment in which the invention is practiced. For example, if the invention is applied in an exercise environment, the interface unit 34 can be a tachometer, ergometer or other device designed to measure the amount of work performed by the subject.

2. Hardware Configuration

Figure 2:
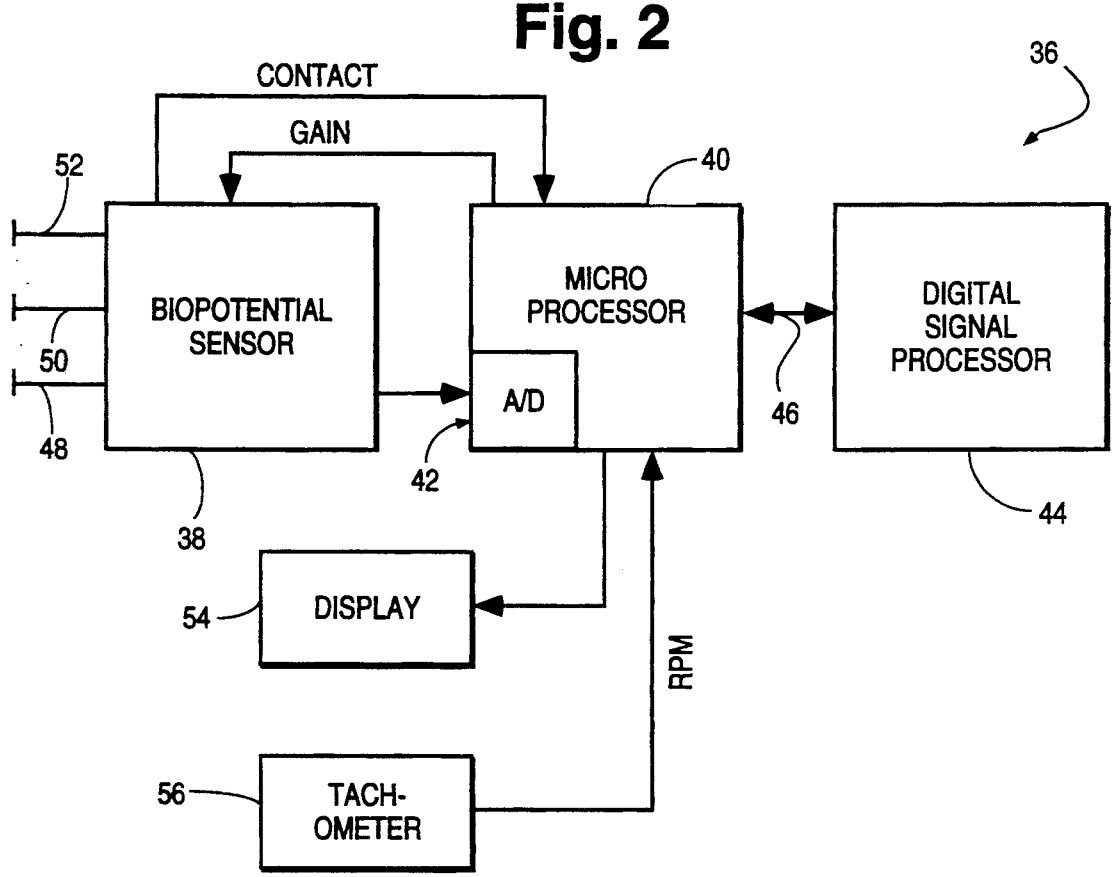
FIG. 2 is a block diagram of the preferred embodiment of the apparatus shown in FIG. 1.

FIG. 2 is a block diagram of a heart rate monitor 36 which embodies the generalized apparatus shown in FIG. 1. The monitor 36 includes a biopotential sensor 38, a microprocessor 40 which is electronically connected to the biopotential sensor 38 via an analog-to-digital convertor 42 ("A/D convertor"), and a digital signal processor 44, which is an ADSP-2105 microcomputer by Analog Devices, of Norwood, Mass., connected via an eight bit serial port interface 46 to the microprocessor 40. The biopotential sensor 38 includes three electrodes 48, 50 and 52. An additional electrode 48a (not shown in FIG. 4A may be included. When used, electrode 48a is electrically coupled to electrode 48. The biopotential sensor 38 and the accompanying electrodes 48, 50 and 52 are described below in greater detail. The microprocessor 40 is a Motorola 68HC05, which is commercially available.

The biopotential sensor 38 is additionally coupled to microprocessor 40 by a CONTACT signal line and a GAIN signal line. The CONTACT signal provides an indication of whether a subject is in physical contact with the electrodes 48, 50 and 52. The GAIN signal provides a control value for controlling the gain of an adjustable gain amplifier which is included (but not shown) in the biopotential sensor 38. The operation of the GAIN signal is described below in connection with FIG. 5. Microprocessor 40 is additionally coupled to a display 54 and an ergometer 56. The display 54 is an LED or like display for displaying the true heart rate as computed by monitor 36. The ergometer 56 may include a tachometer or other device FIG. 3 for measuring the work and rate of work performed by the subject.

Figure 3:
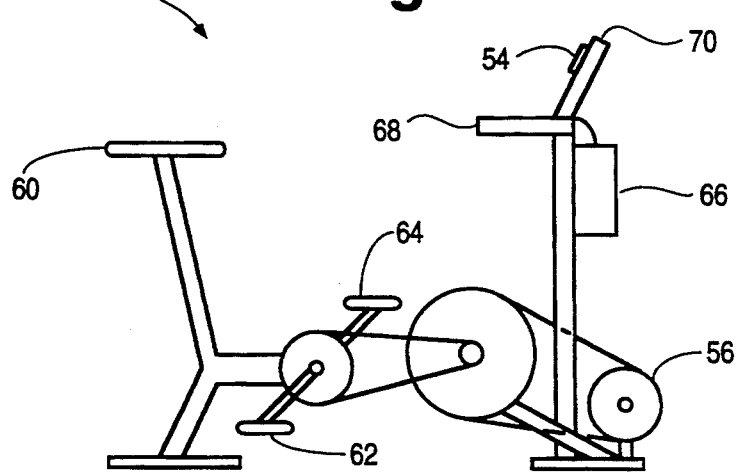
FIG. 3 is a side view of an exercise appliance which incorporates the apparatus of FIGS. 1 and 2.

FIG. 3 illustrates the exercise appliance 58 which, in this case, is a stationary bicycle, that includes a seat 60 and pedals 62 and 64. The purpose of exercise appliance 58 is to provide the user a means of conveniently exercising. To this end, the user sitting on the seat 60 pedals the pedals 62 and 64 which are operatively connected to the ergometer 56. In this case the ergometer 56 is a tachometer which measures the revolutions per minute of the pedals 62 and 64. Other means for measuring the work and rate of work performed by the user are widely known and can be employed. As shown in FIG. 2, the tachometer 56 is operatively associated with microprocessor 40 for providing an RPM signal indicating the speed at which the pedals 62 and 64 are revolving. The exercise bicycle 58 also includes a housing 66, a handlebar 68 and the LED display 54 shown in FIG. 2. The biopotential sensor 38, the microprocessor 40, the A/D converter 42 and the digital signal processor 36 of FIG. 3 are contained (but not shown) in the housing 66. The electrodes 48, 50 and 52 are operatively disposed on the handlebar 68, as described below in greater detail. In practice, the control panel 70 also contains other displays and control buttons for enabling the subject to select a variety of operating modes available on exercise appliance 58. The exercise bicycle 58 is but one example of the types of exercise equipment with which the invention may be applied.

Figure 4A:
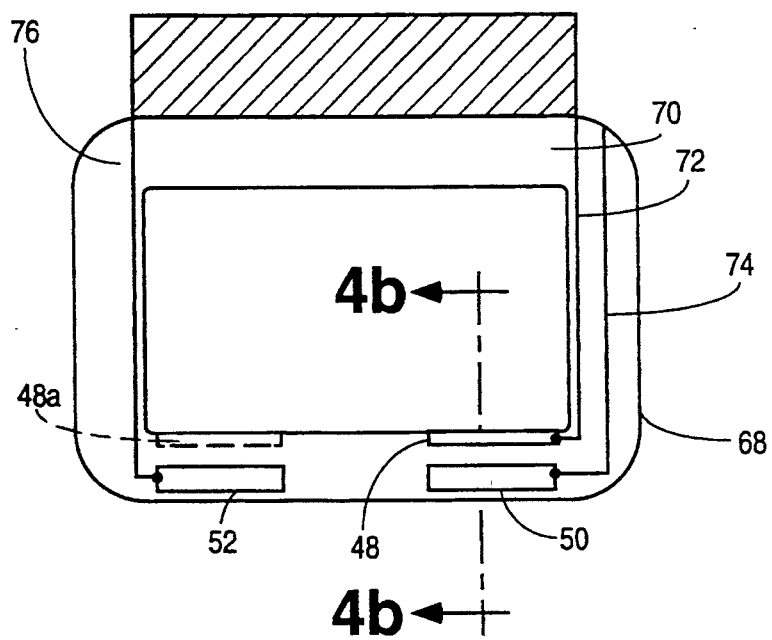
FIG. 4A is a top view of three electrodes mounted onto the handlebars of the exercise appliance shown in FIG. 3.
Figure 4B:
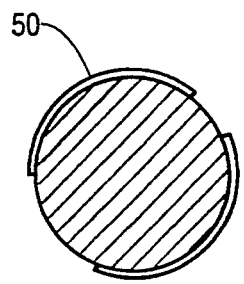
FIG. 4B is a sectional view of the electrodes and handlebars taken along the line A—A' shown in FIG. 4A.

FIG. 4A is a top view of the handlebar 68. FIG. 4B is a cross section view of handlebar 68 taken at the line segment A—A'. As shown in FIGS. 4A and 4B, the handlebar 68 is a cylindrical member which is bent into a rectangular-shaped ring. The electrodes 48, 50 and 52 are preferably rectangular-shaped strips of conductive material, which are mounted upon the handlebar 68 so that their respective longitudinal edges are parallel with the handlebar 68. As shown in FIG. 4A, the electrodes 50 and 52 are positioned along the top side of the handlebar 68 so that they will come into direct physical contact with the palms of the user's right and left hand, respectively, when he grasps the handlebar 68 with both hands. As shown in FIG. 4B, the electrode 48 is juxtaposed with the electrode 50 on the opposing side of the handlebar 68. In this manner, when the user places his hands on handlebar 68, electrode 48 is placed in to contact with the fingers of the user's right hand. Each electrode 48, 50 and 52 is electrically coupled to the biopotential sensor 38 by a wire 72, 74 and 76, respectively. Other types of electrode and handlebar arrangements can also be employed. For example, the additional electrode 48a (shown in FIG. 4A with broken lines) may be juxtaposed with electrode 52 on the opposing side of the handlebar 68. As explained above, electrodes 48 and 48a are electrically coupled.

Figure 5:
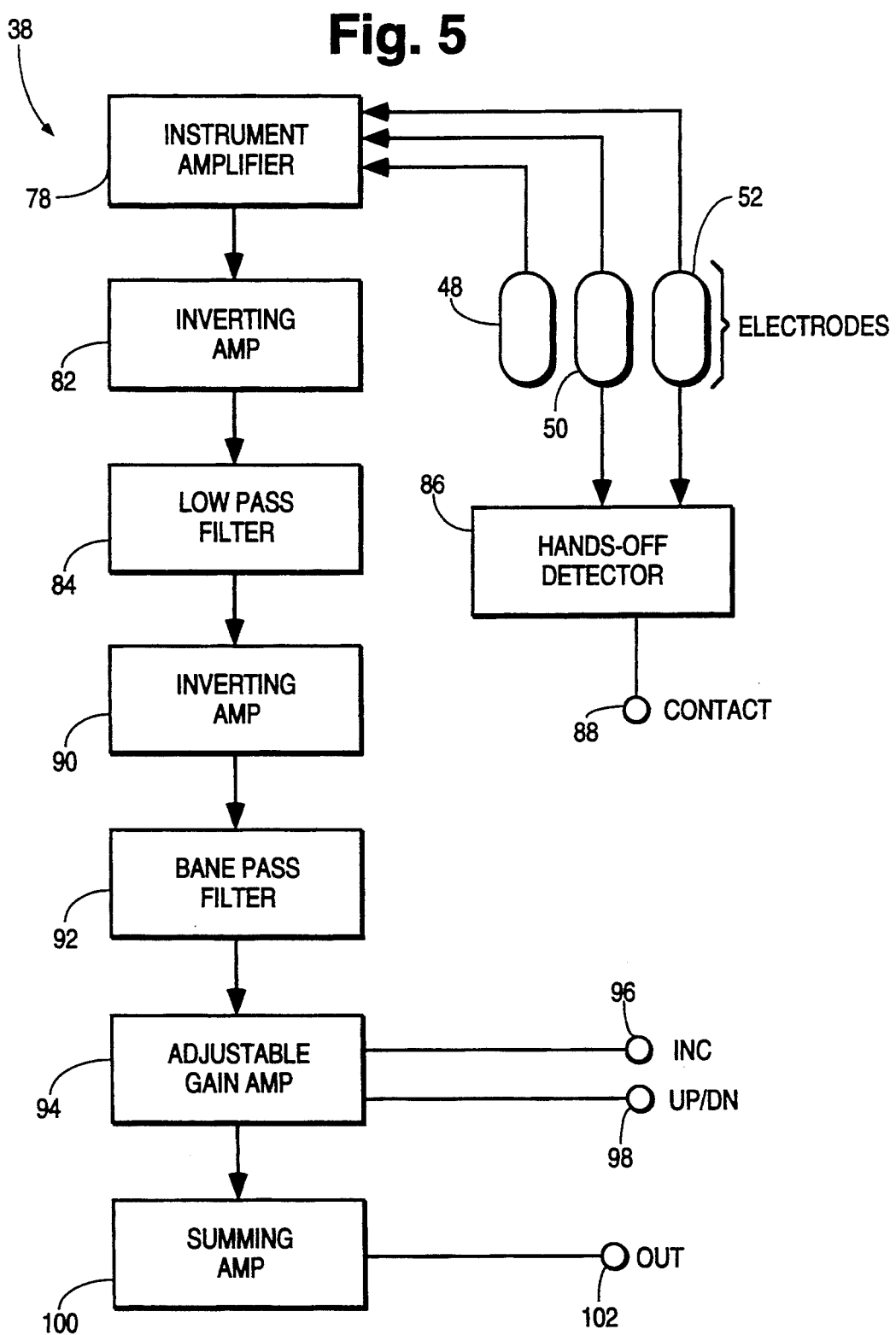
FIG. 5 is a block diagram of the biopotential sensor of the apparatus shown in FIG. 2.
Figure 6:
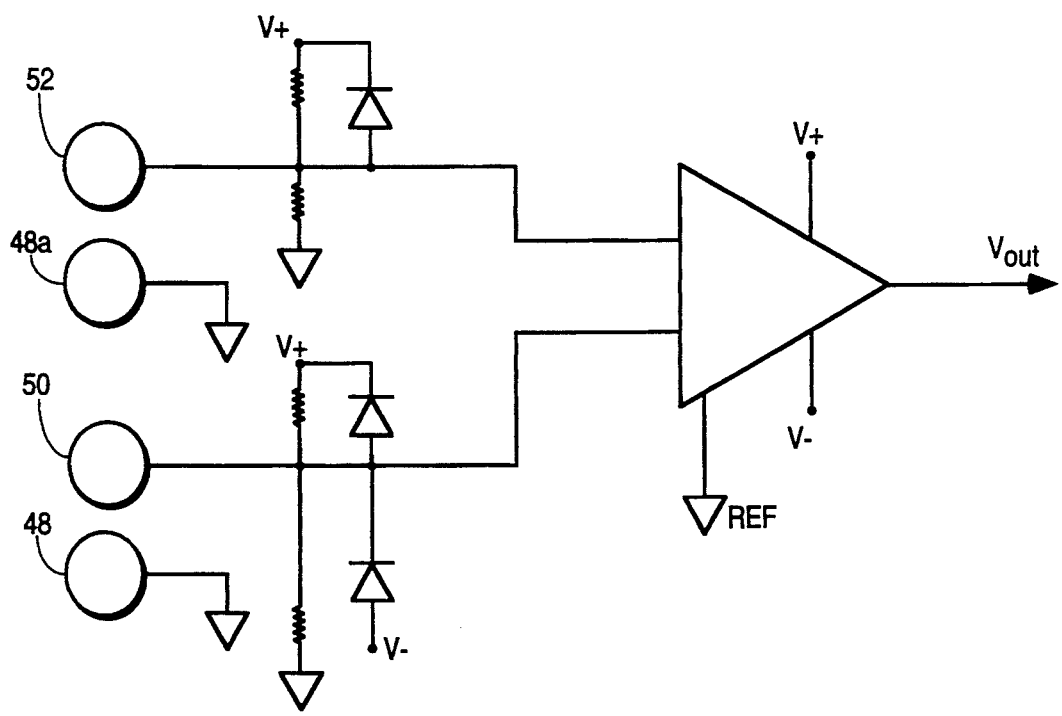
FIG. 6 is a schematic diagram of the electrodes and instrument amplifier of the biopotential sensor shown in FIG. 5.

FIG. 5 is a block diagram illustrating the biopotential sensor 38 in greater detail. When the user grasps the handlebar 68, his hands come into contact with the electrodes 48, 50 and 52 as described above. In this manner, an electric circuit is closed between electrodes 50 and 52 through the user's body, and a voltage potential (i.e., the biopotential) is created across the electrodes 50 and 52. The origin of this voltage potential is the bioelectric activity of the user's muscles, including the heart. With particular types of equipment including stair climbing machines and treadmills, better results have been obtained when both electrodes 48 and 48a are used, and both are tied to ground (preferably the metal frame of exercise appliance 58, if practicable). Each of the electrodes 48, 50 and 52 is electrically coupled to an instrument amplifier 78. Instrument amplifier 78 is shown in greater detail in FIG. 6. The output of the instrument amplifier 78 is electronically coupled to an inverting amplifier 82. The output of the inverting amplifier 82 is electronically coupled to a low pass filter 84.

Figure 7:
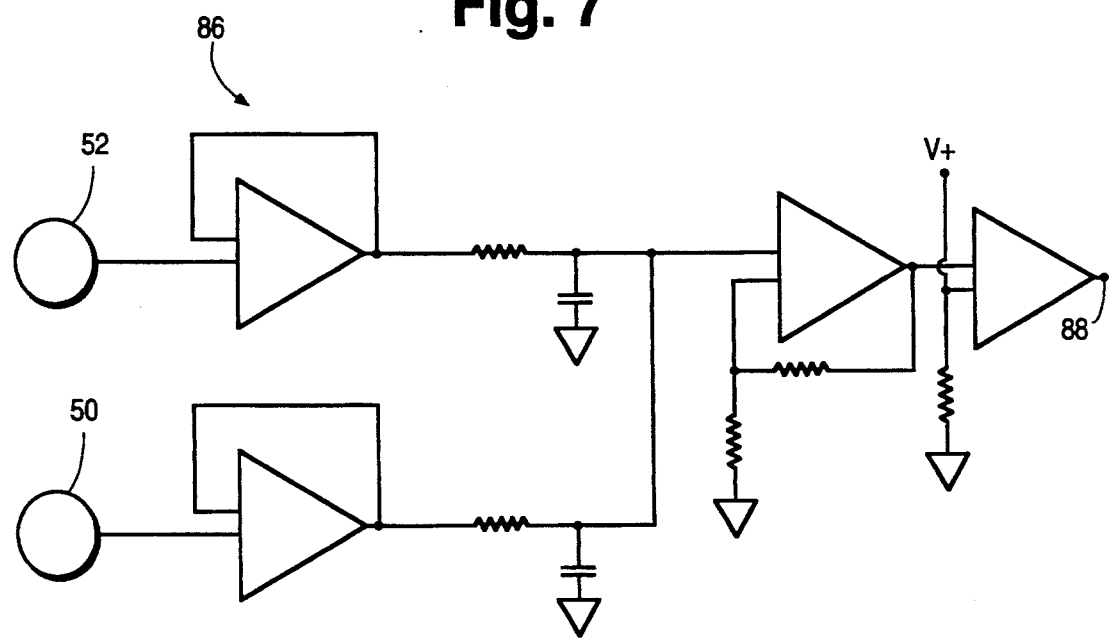
FIG. 7 is a schematic diagram of the hands-off detector circuit of the biopotential sensor shown in FIG. 5.

Additionally, the electrodes 50 and 52 are coupled to a hands-off detector 86 (best seen in FIG. 7). The output of hand-off detector is the external signal CONTACT generated at a terminal 88. When the user removes his hands from the handlebar 68, the hands-off detector 86 causes the CONTACT signal to go to a low voltage (or logical "low") state on the terminal 88, and when the user places his hands on the handlebar 68, the hands-off detector 86 causes the CONTACT signal to be at a high voltage (or logical "high") state.

The output of the low pass filter 84 is applied to an inverting amplifier 90 and the output of the inverting amplifier 90 is input to a band pass filter 92. The output of the band pass filter 92 is electrically coupled to an adjustable gain amplifier 94. The adjustable gain amplifier is a conventional circuit which is responsive to a pair of external digital signals INC and UP/DN, which are applied to the adjustable gain amplifier 94 over a pair of terminals 96 and 98, respectively. The adjustable gain amplifier 94 operates so that when the UP/DN signal is at a logical high, the gain of the adjustable gain amplifier 94 is incremented by a predetermined amount each time the INC signal is strobed. Conversely, when the UP/DN signal is at a logical low state, the gain of the adjustable amplifier 94 is decremented by a predetermined amount each time the INC 30 signal is strobed. For simplicity, the INC and UP/DN signals are show collectively as the GAIN signal in FIG. 2. The output of adjustable gain amplifier 94 is coupled to a summing amplifier 100 and the output of the summing amplifier 100 is made available at a terminal 102.

3. Data Acquisition and Communication

Figure 9:
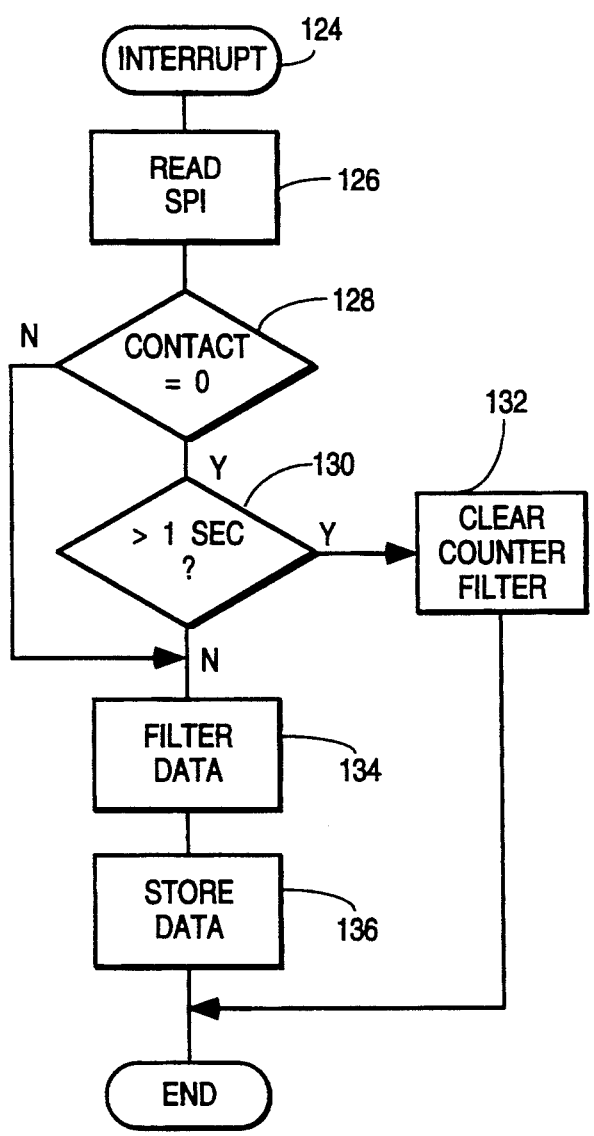
FIG. 9 is a logic flow chart illustrating the input/output operation of a digital signal processor of the apparatus shown in FIG. 2.
Figure 10:
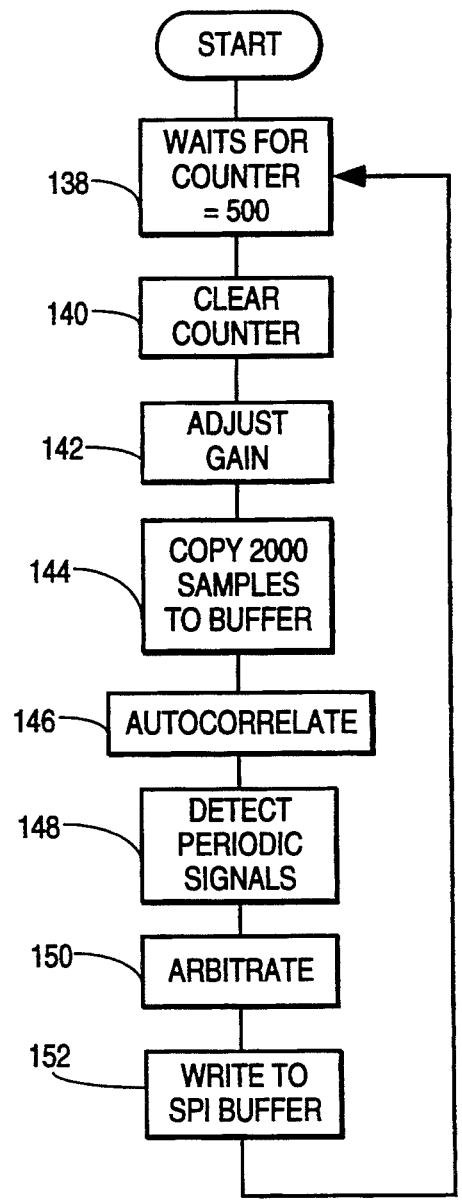
FIG. 10 is a logic flow chart illustrating the operation of the digital signal processor of the apparatus shown in FIG. 2.
Figure 11:
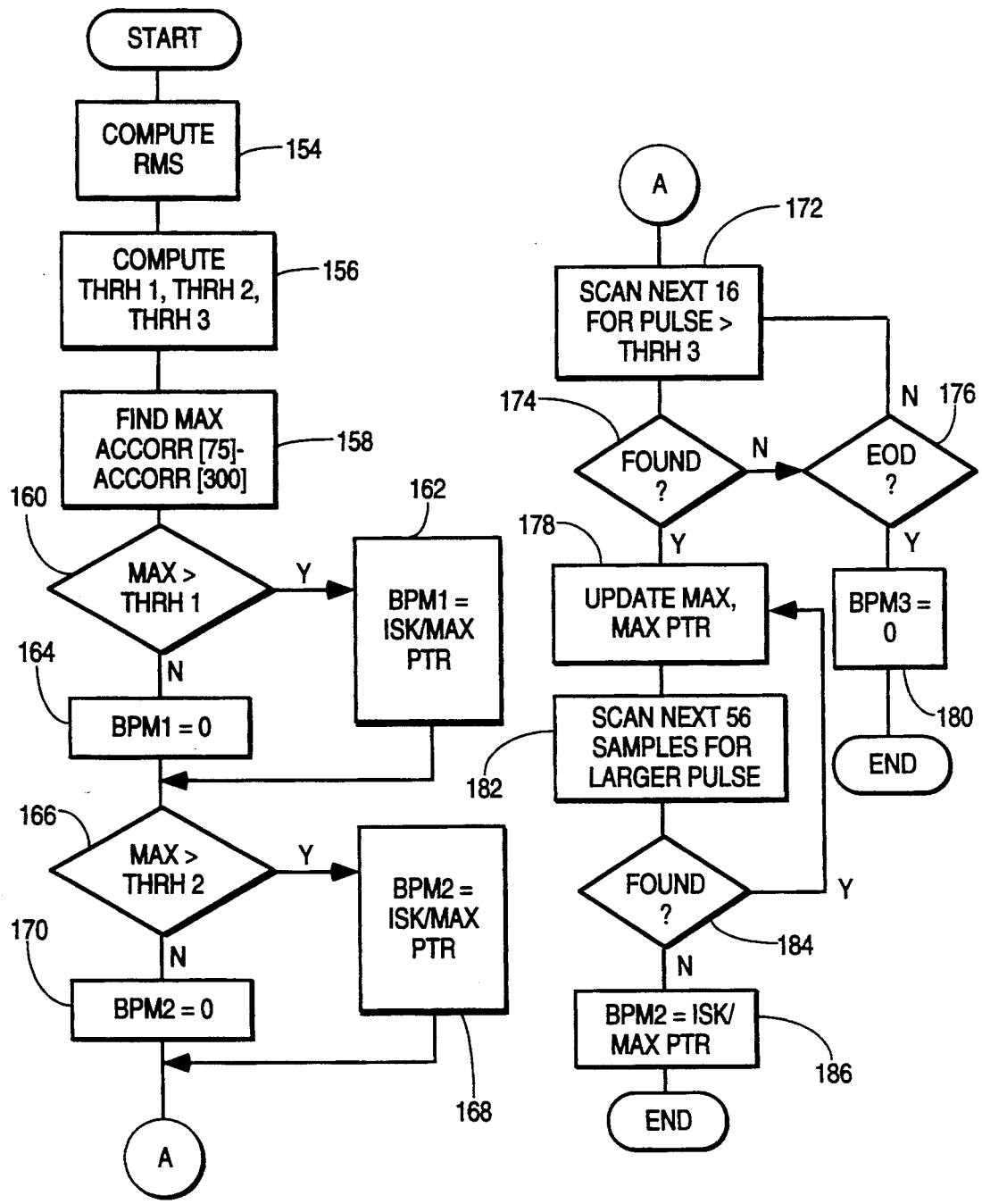
FIG. 11 is a logic flow chart illustrating the signal indication operation of the digital signal processor of FIG. 2 in accordance with a first signal indication technique.

The operation of the monitor 36 may be understood by reference to the block diagram of FIG. 1. Each of the functions of the apparatus 20 is implemented in the monitor. Thus, the biopotential sensor 22, as shown in FIG. 1, is implemented in the biopotential sensor 38 and the electrodes 48, 50, 52. The filter/amplifier 24, as shown in FIG. 1, is also included in the biopotential sensor 38. Preferably, additional filtering is performed by the digital signal processor 44. The autocorrelator 26, the signal processor 28 and the arbitrator 30, as shown in FIG. 1, are implemented in the digital signal processor 44, the operation of which is illustrated in FIGS. 9-11. The external data interface unit 34, as shown in FIG. 1, is implemented by the tachometer 56, and the display 32, as shown in FIG. 1, is implemented by the display 54.

In the preferred embodiment, the output of the biopotential sensor 38 is converted from an analog to a digital signal by the A/D converter 42 and then used by the digital signal processor 44. The microprocessor 40 functions as an input/output interface between the A/D converter 42 and the digital signal processor 44.

Figure 8:
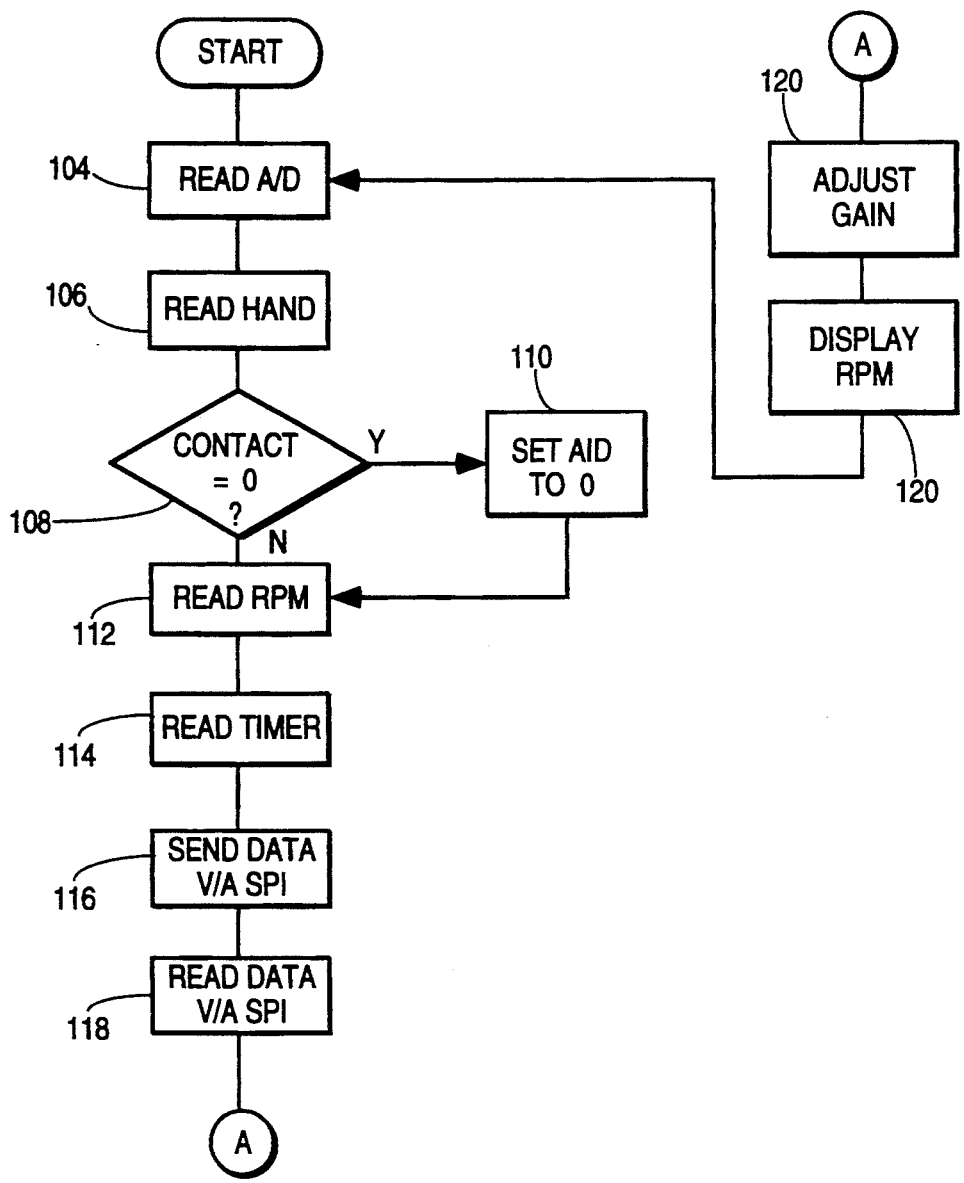
FIG. 8 is a logic flow chart illustrating the operation of a microprocessor in the apparatus shown in FIG. 2.

FIG. 8 is a logic flow chart illustrating the operation of microprocessor 40. Beginning at a block 104, the microprocessor 40 stores the output of the A/D converter 42, thereby capturing a digital sample of the analog value of the output of the biopotential sensor 38. As described below, microprocessor 40 preferably samples the A/D converter output 42 every four milliseconds. For convenience, the operation performed at the block 104 is referred to as a "sample". Then, at a block 106, microprocessor 40 stores the status of the CONTACT signal. At a decision block 108, if the microprocessor 40 determines that the value of the CONTACT signal is zero (indicating that the user's hands are off the electrodes 48, 50 and 52), then control moves to a block 110. Otherwise, control moves to a block 112. At block 110, the microprocessor 40 sets the stored value of the A/D converter 42 to zero, and then moves to a block 112.

At the block 112, the microprocessor 40 stores the value of the RPM signal, which is generated by the tachometer 56. At a block 114, the microprocessor 40 stores the value of a timer (not shown). The timer measures the amount of time which the user has been operating the exercise appliance 58. The timer is reset whenever the RPM signal has a zero value. Control then moves to a block 116 where the microprocessor 40 sends a data packet to the digital signal processor 44 via serial port interface 46.

The data packet comprises the following eight bytes (but other communication protocols may be used):
1. STX (start-of-data flag)
2. gain status
3. A/D sample data
4. RPM
5. elapsed time
6. hands on/off indication
7. checksum of the first six bytes
8. ACK or NAK The calculation of the checksum which is transmitted in byte six may be performed according to any one of numerous, widely-known techniques. Similarly, the communications protocol bytes STX, ACK and NAK can be provided in accordance with a conventional communication protocol. The hands on/of indication corresponds to the value of the CONTACT signal. The A/D sample data is the value of the stored output of the A/D converter 42. Gain status indicates the value of the command which has been most recently implemented.

At a block 118, the microprocessor 40 reads a data packet from a serial port interface buffer (not shown) of the digital signal processor 44. Preferably, the data packet read from the digital signal microprocessor 44 comprises the following eight bytes:
1. STX (start-of-data flag)
2. computed value of heart rate
3. gain command
4. zero
5. zero
6. zero
7. checksum of the first six bytes
8. ACK or NAK Control then moves to a block 120, where the microprocessor 40 operates to adjust the gain of the adjustable gain amplifier 94 in accordance with the gain command contained in the third byte of the data packet which the microprocessor 40 reads at the block 118. As indicated above, the adjustable gain amplifier 94 is a component of the biopotential sensor 38, and is responsive to the external digital signals INC and UP/DN (as shown in FIG. 5), which are collectively shown as the GAIN signal in FIG. 2. At a block 122, the microprocessor 40 displays on display 54 the value of the computed heart rate which is contained in byte two of the data packet read in the block 118.

Upon completion of step 122, control returns to the block 104, where the steps 104 through 122 are repeated. This sample cycle is repeated every four milliseconds. In this manner, the microprocessor 40 functions as an input/output interface between the digital signal processor and the biopotential sensor 38, the display 54 and the tachometer 56.

The user's heart rate is computed by the digital signal processor 44, the operation of which is illustrated by the logic flow charts set forth in FIGS. 9–19. FIG. 9 illustrates an interrupt routine which is invoked when microprocessor 40 sends the data packet via the serial port interface 46 to digital signal processor 44. At an interrupt block 124, the digital signal processor 44 suspends its other processing activity as described below in connection with FIG. 10. Control then moves to a block 126, where the digital signal processor 44 reads the data packet sent by microprocessor 40. At decision block 128, microprocessor 40 determines whether the hands on/off indication, contained in byte six of the data packet and corresponding to the value of the CONTACT signal, is equal to zero.

If the hands on/off indication is equal to zero, control moves to a decision block 130. Otherwise control moves to a block 134. At the decision block 130, if the hands on/off indication has been zero for more than a predetermined time, preferably one second, then control moves to a block 132. Otherwise control continues to the block 134. The determination as to whether one second has elapsed is made by use of a timer (not shown) within the digital signal processor 44, which is reset whenever the value of the hands on/off indication goes to zero. At the block 132, the digital signal processor 44 clears a counter and a digital filter (not shown), the operation of which are discussed below.

At the block 134, the digital signal processor 44 passes the incoming A/D sample data, contained in byte three of the data packet received from the microprocessor 40 at the block 126, through the above-mentioned digital filter. Preferably, the digital filter is a low-pass Bessel IIR digital filter, for which the center frequency is 10 Hz, the bandwidth is 20 Hz, the transition band is 50 Hz, and the stopband attenuation is approximately 50 Db at 70 Hz. Control then moves to a block 136 where the digital signal processor 44 stores the filtered A/D digital sample in a circular buffer. The buffer has at least 2,500 data elements. For a four millisecond sample cycle, the buffer will hold A/D sample data taken over a 10 second period.

4. Computation of Heart Rate

Referring to FIG. 10, the operation of the digital signal processor 44 in determining heart rate is illustrated. As discussed above, a counter (not shown) is operatively associated with the digital signal processor 44 for counting the number of times A/D sample data is read into the circular buffer. At a block 138, the digital signal processor 44 waits for the counter to reach a predetermined value (preferably, 500). In this case, 500 A/D samples represent data taken over a two second period on "window". When the counter reaches the predetermined value, control moves to a block 140, where the counter is cleared. At a block 142, the contents of the circular buffer are inspected to find the peak value of A/D sample data within the two-second window. If the peak value indicates a voltage outside of a predetermined range (preferably, between 4.5 volts and 4.75 volts out of a maximum five volts), the gain of the adjustable gain amplifier 94 is adjusted so that peak voltage falls within the predetermined range. This adjustment is accomplished by generating a gain adjustment command, which is discussed below in greater detail.

At a block 144 of FIG. 10, a predetermined number of samples (preferably, 2000) are copied from the circular buffer into a work buffer. The work buffer is preferably an array of 2000 data storage elements. At block a 146, an autocorrelation is performed on the contents of the work buffer. The autocorrelation is preferably implemented by computing the value of $R_k$ over k equal to 1 through N, where N is preferably 400, according to the following formula:

$$R_k = \sum_{m=0}^{N-1-k} S_m' S_{(m+k)}$$

where $S_m$ equals value of the A/D sample data in the $m^{th}$ element of the work buffer. The values of $R_k$ are stored in an autocorrelation output buffer, which is preferably an array of data storage elements R[0] through R[N]. Thus, $R_k$ is the value stored in the $k^{th}$ element of the autocorrelation output buffer. The block 146 represents the function performed by the autocorrelator 26 shown in FIG. 1.

At a block 148 of FIG. 10, the digital signal processor 44 conducts one or more examinations on the contents of the autocorrelation output buffer to detect the presence of periodic signals that could correspond to heartbeat. Each examination utilizes a different technique to scan the autocorrelation output buffer for the indication of a periodic signal which corresponds to heartbeat. For each examination, the digital signal processor 44 generates one or more candidate heart rate signals. For clarity, it should be noted that the block 148 implements the function of the signal processor 28 shown in FIG. 1. The function performed at block 148 is described in greater detail below in connection with FIG. 11.

In some cases, the detection of block 148 will yield a plurality of candidate heart rate signals. At a block 150 of FIG. 10, the digital signal processor 44 performs the arbitration function by selecting one of these candidate heart rate signals as the true (or "arbitrated") heart rate. This selection is performed in accordance with certain predetermined criteria, including reasonableness criteria. These criteria can include the elapsed time which the user has been operating the exercise appliance 58, the value of the RPM signal (which indicates the effort being expended by the user), and the value of the previously selected candidate heart rates. If none of the candidate heart rate signals is acceptable, then the value of a previously selected (and preferably, most recent) signal arbitrated heart rate is used.

Computer routines may be used to implement the foregoing functions. The exact nature of these routines depends on the particular embodiment in which the invention is implemented. A computer routine which is particularly well-suited for use with stair climbing machines and treadmills is discussed in more detail below.

At a block 152, the digital signal processor 44 writes a data packet to its serial port interface buffer (not shown). As discussed above, the microprocessor 40 via the serial port interface 46. As discussed above, the data packet sent to the microprocessor 40 comprises eight bytes, including a byte containing the value of the arbitrated heart rate. It is this value which the microprocessor 40 transmits to display 54 and which is visible to the user. In some cases, superior results may be obtained by placing the arbitrated heart rate in a buffer and calculating the average value of the last N arbitrated heart rates (where N is a suitable number such as 5). It is this average value that can then be sent to microprocessor 40 for display to the user. Thus, for purposes of this specification, the term "arbitrated" heart rate should be distinguished from "displayed" heart rate when the displayed heart is a running average of the arbitrated heart rates.

5. Detection of Candidate Signals

Referring to FIG. 11, the operation of digital signal processor 44 at the block 148 is described in greater detail. At block 154 the digital signal processor computes the root-mean-square ("RMS") value of the autocorrelation output buffer. At block 156, three threshold values (THRH1, THRH2, and THRH3) are computed. The first threshold value (THRH1) is equal to the RMS value multiplied by a first constant (preferably one). The second threshold value (THRH2) is set equal to the RMS value multiplied by a second constant (preferably equal to 1.25). The third threshold value (THRH3) is set equal to a percentage (preferably, 20%) of the largest value (typically the first element) of the autocorrelation output buffer.

At a block 158 the digital signal processor 44 searches for a peak value within a predetermined range of the autocorrelation output buffer. Preferably, this range is from the 75th element to the 300th element. At a decision block 160 this peak value is compared to the first threshold value (THRH1). If the peak value is greater than THRH1, control moves to a block 162. otherwise control continues to a block 164 where the first candidate heart rate (BPM1) is set equal to zero. At the block 162 the first candidate heart rate (BPM1) is set equal to a constant divided by P, where P is the pointer to that element of the autocorrelation output buffer which contains the peak value found in the block 158. Preferably the constant equals the number of samples per minute. In the preferred embodiment, the analog output of the biopotential sensor 38 is sampled every four 20 milliseconds by the microprocessor 40. Thus, 250 samples are taken each second, and 15,000 samples are taken each minute. In this case, the predetermined constant equals 15,000. For example, if at the block 158 a suitable peak value is found at the 100th element of the autocorrelation buffer array, the value of P is equal to 100. Accordingly, BPM1 is set equal to 15,000 divided by 100, or 150 beats per minute.

Upon completion of the block 162 (or the block 164, as the case may be), control moves to decision block 166. At the decision block 166, if the maximum value computed at 30 the block 158 is greater than or equal to the second threshold value (THRH2), then control moves to a block 168. Otherwise control continues to a block 170. At the block 170 the second candidate heart rate (BPM2) is set to zero. At the block 168, the second candidate heart rate (BPM2) is set to a predetermined constant divided by P, as described above.

After completion of processing at the block 170 or 168 the program continues to block 172. At the block 172, the digital signal processor 44 begins scanning the autocorrelation output buffer for a pulse with a waveform which is characteristic of a heartbeat (a "characteristic pulse"). Such pulses are identified by pulse height, width and shape. The characteristic pulse shape is a local peak between, and in close proximity to, two local minimums. The characteristic pulse width is within a predetermined range (preferably, between 14 and 18 autocorrelation output buffer elements). The characteristic pulse height is greater than the third threshold value (THRH3). The concepts of pulse height and width are described below in connection with FIG. 13.

This scanning takes place within a predetermined range (or "data window") of the autocorrelation output buffer (preferably between the 75th and 300th elements). The buffer is scanned in blocks of predetermined size (preferably 16 buffer elements). Thus, in its first iteration, the digital signal processor 44 will search the 75th through 90th elements of the autocorrelation output buffer for a characteristic pulse. At decision block 174, if a characteristic pulse is not found, control moves to a decision block 176. Otherwise control continues to a block 178. At the block 176, if the digital signal processor 44 has reached the end of the data window, control moves to block 180, where the third candidate heart rate (BPM3) is set to zero and processing terminates. If the digital signal processor 44 has not reached the end of the data window, control returns to the block 172, where the digital signal processor 44 scans the next sixteen data elements for a characteristic pulse.

At the block 174, if a characteristic pulse has been located, then control moves to the block 178. It will be noted that the peak value of the located pulse will reside in an element of the autocorrelation output buffer. At the block 178, the index (or "pointer") to that element is stored in the variable P. For convenience, the value of pulse height is stored in the variable MAX. Thus, if the characteristic pulse has a pulse height of 4.25 and its peak is located at the 100th element of the output buffer, than P is set to the value 100 and MAX is set to the value 4.25.

Control then moves to a block 182 where the digital signal processor 44 scans the next 56 elements past the $p^{th}$ element, searching for a characteristic pulse which has a larger pulse height than the pulse height currently saved in MAX. At decision block 184, if such a larger pulse is found, then control returns to the block 178. At the block 178, the values of P and MAX are updated with the pointer and pulse height, respectively, of the newly-found pulse, and the 15 scanning process at the block 182 is repeated. Otherwise control continues to the block 186, where the third candidate heart rate (BPM3) is set equal to a predetermined constant divided by P. Preferably, the predetermined constant equals the number of samples per minute. With respect to the arbitration function described above, the third candidate heart rate (BPM3) is generally more reliable than the first and second candidate heart rates (BPM1 and BPM2, respectively) and should be selected in the event that all other reasonableness criteria do not lead to a successful arbitration.

Figure 12:
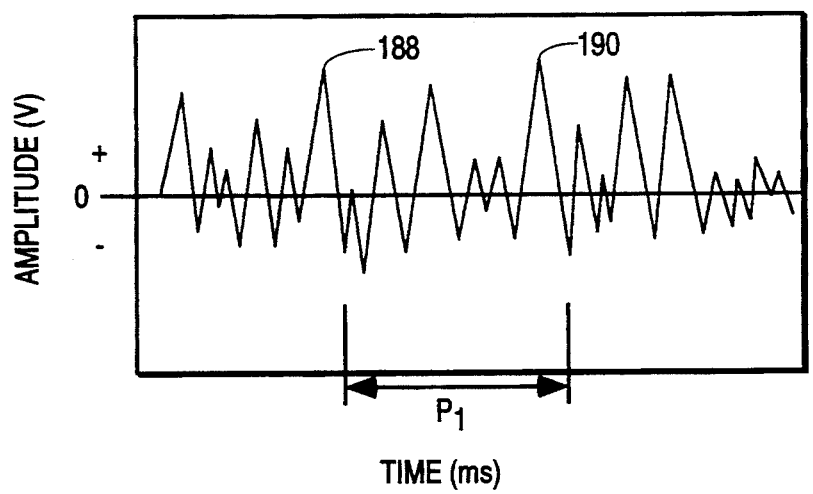
FIG. 12 is graph of the output in volts of the biopotential sensor shown in FIG. 5, as measured against time in milliseconds.
Figure 13:
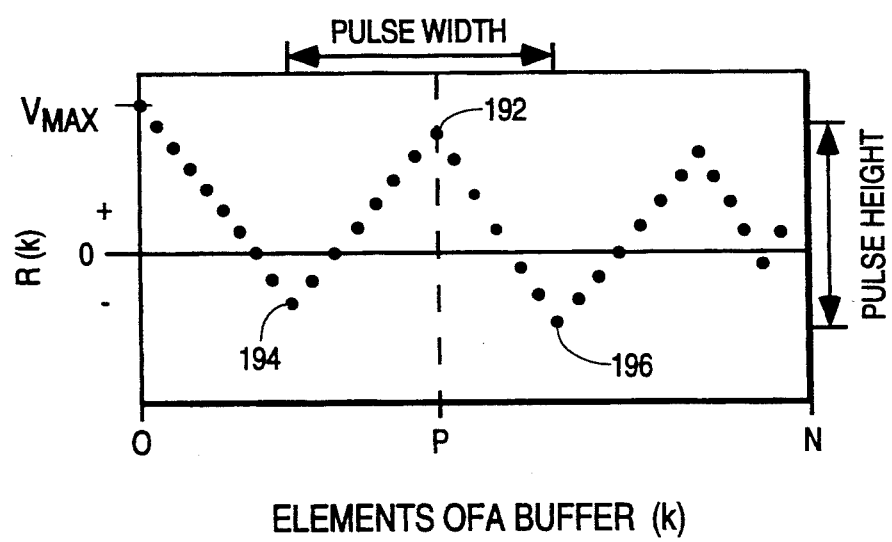
FIG. 13 is a graph of the digital output of the autocorrelation performed by the digital signal processor of the apparatus shown in FIG. 2.

Understanding of the operation of the invention is enhanced by reference to FIGS. 12 and 13. FIG. 12 is a graph of the raw ECG output of the biopotential sensor 38 over time, measured in volts. As described above, this output is periodically digitized and sampled by the microprocessor 40 in cooperation with the A/D converter 42. As FIG. 12 illustrates, the output of the biopotential sensor 38 is a noisy signal with peaks shown at 188 and 190. For the purposes of this illustration, it is assumed that the peaks 188 and 190 are each indicative of a heartbeat of the user. Under this assumption, the heart rate is inversely proportional the time period P1 between the peaks 188 and 190.

After the output of the biopotential sensor 38 is digitized and sampled, it is read by digital signal processor 44 via the serial interface 46 as described above. As described above, digital signal processor 44 performs an autocorrelation at the block 146 on the digitized signal.

FIG. 13 is a graph of the results of this autocorrelation. As discussed above, the autocorrelation 10 output is stored in a buffer array. In the graph depicted in FIG. 13, the horizontal axis shows k, the pointer to each element in the autocorrelation output buffer. The vertical axis shows $R_k$, the value contained in the $k^{th}$ element of the autocorrelation output buffer. As the graph indicates, the largest value of $R_k$ is found in the first element of the autocorrelation output buffer. However, a local peak 192 and local minimums 194 and 196 also exist. It will be observed that the local peak 192 is contained in the $p^{th}$ element of the autocorrelation output. Of general interest is the fact that, mathematically speaking, P is also the displacement (measured in samples) used in the autocorrelation to compute $R_k$. As described above in connection with FIG. 11, the digital signal processor 44 computes the third candidate heart rate (BPM3) by dividing a predetermined constant (preferably, 15,000) by P, the pointer to the local peak 192.

For purposes of this illustration, it is assumed that the waveform characterized by the local peak 192 and local minimums 194 and 196 is characteristic of the user's heartbeat. In this case, "pulse width" is equal to the horizontal distance between the local minimums 194 and 196, as indicated in FIG. 13. "Pulse height" is the vertical distance between the local peak 192 and the local minimums 194 and 196. A "peak" such as local peak 192 is measured by its vertical distance from "zero."

It will be noted that in the disclosed embodiment, the analog biopotential signal is scaled between 0.0 and 5.0 volts. Thus, the baseline voltage is 2.5 volts. In effect, voltage values of 2.5 volts are considered "zero", and voltage values between 0.0 and 2.5 volts are considered "negative". It should also be noted that these analog values are represented digitally as integers having a value between 0 and 255, with a baseline (or "zero") value of 128.

6. Alternative Techniques for Detecting Candidate Signals

Figure 14:
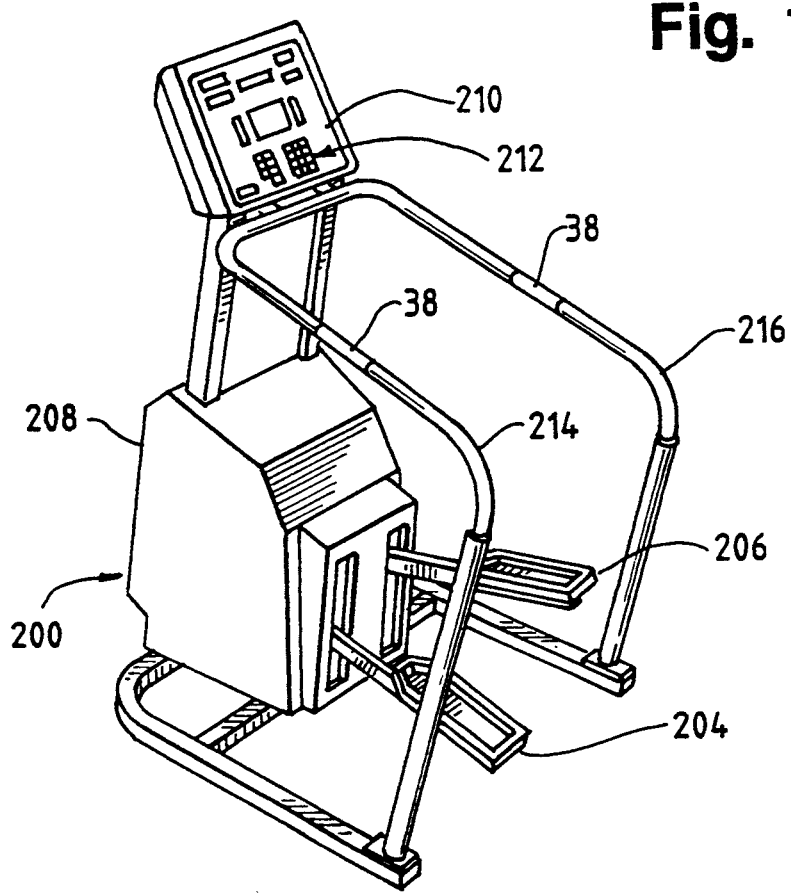
FIG. 14 is a perspective view of a stair climbing exercise machine which incorporates the heart rate monitor of FIG. 2.
Figure 15:
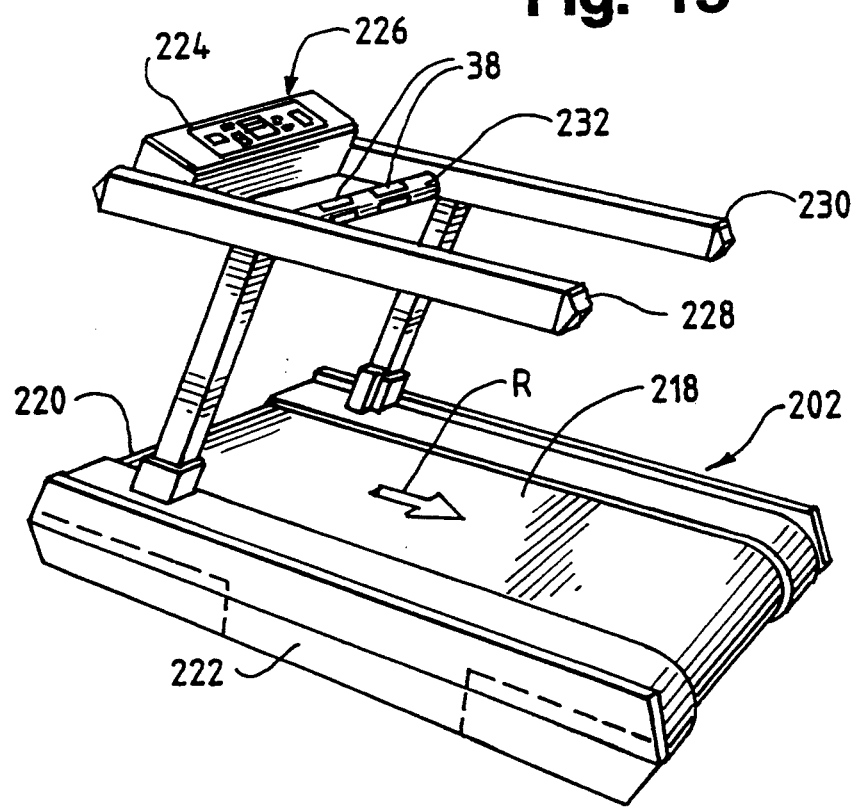
FIG. 15 is a perspective view of a treadmill exercise machine which incorporates the heart rate monitor of FIG. 2.

As indicated above, the invention may be practiced with stationary bicycles and other types of exercise equipment. For example, as shown in FIG. 14, the invention may be practiced with a stair climbing machine 200. Alternatively, the invention could be practiced with a treadmill 202, as shown in FIG. 15. Suitable stair climbers and treadmills are disclosed in U.S. patent application Ser. Nos. 07/658,156 (filed Feb. 20, 1991) and 07/686,906 (filed Apr. 17, 1991) and U.S. Pat. No. 5,135,447, the disclosures of which are hereby incorporated by reference in their entirety.

The purpose of stair climbing machine 200 is to provide the user a means of aerobic exercise. To this end, the user stands on vertically reciprocating foot pads 204 and 206. Food pads 204 and 206 are drivingly connected to a transmission (shown generally at 208) which converts (via a one way clutch or the like) the vertically reciprocating motion of pedals 204 and 206 into a rotational motion. This rotational motion is then resisted by an a load device (not shown) to provide exercise resistance. The load device may be an alternator, eddy current break or band break. The ergometer 56 is operatively coupled to the transmission 208 for measuring the rate at which the user exercises. In this case, ergometer 56 is a tachometer which measures the rotational speed of transmission 208. Other techniques for measuring work or speed are widely known and can be employed. The heart rate monitor 36 as described above is located within the housing 210 of a control panel 212. Biopotential sensor 38 is mounted to handle bars 214 and 216 (as shown in a generalized manner in FIG. 14). The electrodes 48, 48a, 50 and 52 of biopotential sensor 38 are mounted to handle bars 214 and 216 to engage the user's hand in the same manner as described above in connection with FIGS. 4A and 4B.

Referring to FIG. 15, the purpose of treadmill 202 is also to provide the user a means of aerobic exercise. To this end, the user stands on endless belt 218 which is driven by a motor (not illustrated) in the direction indicated by arrow R. As the belt 218 passes below the user, he or she walks or runs in place. The user's exercise resistance may be modulated by either increasing the speed of moving belt 218, or placing the belt at an incline by elevating the front end 220 of frame 222. In either case, the ergometer 56 is adapted to detect the incline and/or belt speed, and thereby determine the amount of work being performed by the user. The heart rate monitor 36 as described above is located within the housing 224 of a control panel 226. Two horizontal guardrails 228 and 230 are spaced in parallel relation on opposing lateral sides of moving belt 218. A handlebar 232 is mounted to facing side of guardrails 228 and 230 and extends in a direction transverse to the longitudinal extent of the guardrails 228 and 230. The electrodes of biopotential sensor 38 are mounted to handlebar 232, as shown generally in FIG. 15.

In practicing the invention with stair climbers and treadmills, it is especially difficult to isolate the user's heart rate. To overcome these difficulties, Applicants have provided an alternative technique for detecting the indications of periodic signals in the autocorrelation output at block 148 of FIG. 10. This alternative technique is illustrated more fully in FIG. 16. Beginning at a block 234, the digital signal processor 44 filters the autocorrelation output for the indications of periodic signals in accordance with a plurality of filter criteria. These filter criteria are described below in greater detail, but essentially reduce the autocorrelation signal to a plurality of candidate signals, each of which meets the filter criteria. The number of candidate signals can vary depending on the particular autocorrelation output because any pulse in the autocorrelation output which meets the filter criteria is selected to be a candidate signal. The digital signal processor stores the candidate signals in a candidate array, in which each candidate signal is represented by its peak-to-trough pulse height and its frequency (as expressed in beats per minute). The candidate signals are sorted in descending order of frequency. The digital signal processor 44 then performs an arbitration function to select one of the candidate heart rate signals generated by the signal indication operation.

In one embodiment, the filtering criteria are: (i) pulse height greater than a threshold value THRH3 (defined above); (ii) pulse width of between 14 and 18 autocorrelation buffer elements; (iii) pulse shape that is a local peak between (and in close proximity to) two local minimums; and (iv) a pulse that is substantially vertically symmetrical. As used in the preceding sentence, the terms "pulse height," "pulse width" and "pulse shape" are defined above in connection with FIGS. 12 and 13. Notably "pulse height" means the amplitude of the pulse as measured from local maximum ("peak") to local minimum ("trough"). The term "substantially vertically symmetrical" means that no more than sixty-seven percent of the pulse height is positive or negative. In other words, the amplitude of the pulse is roughly centered about the baseline or "zero" value.

Pulses in the autocorrelation output which meet all four filtering criteria are selected as candidate signals. The frequency and pulse height of each selected pulse are stored and sorted in the candidate array. In practice, the candidate array or list should accommodate at least thirty candidate signals. It has been found that the vertical symmetry filtering criteria can in some cases be eliminated for improved sensitivity and performance. In particular, where both electrode 48 and 48a are used in biopotential sensor 38 and are grounded to the metal frame of an exercise apparatus such as stair climber 200 or treadmill 202, acceptable results may be obtained without the vertical symmetry criteria.

Figure 16:
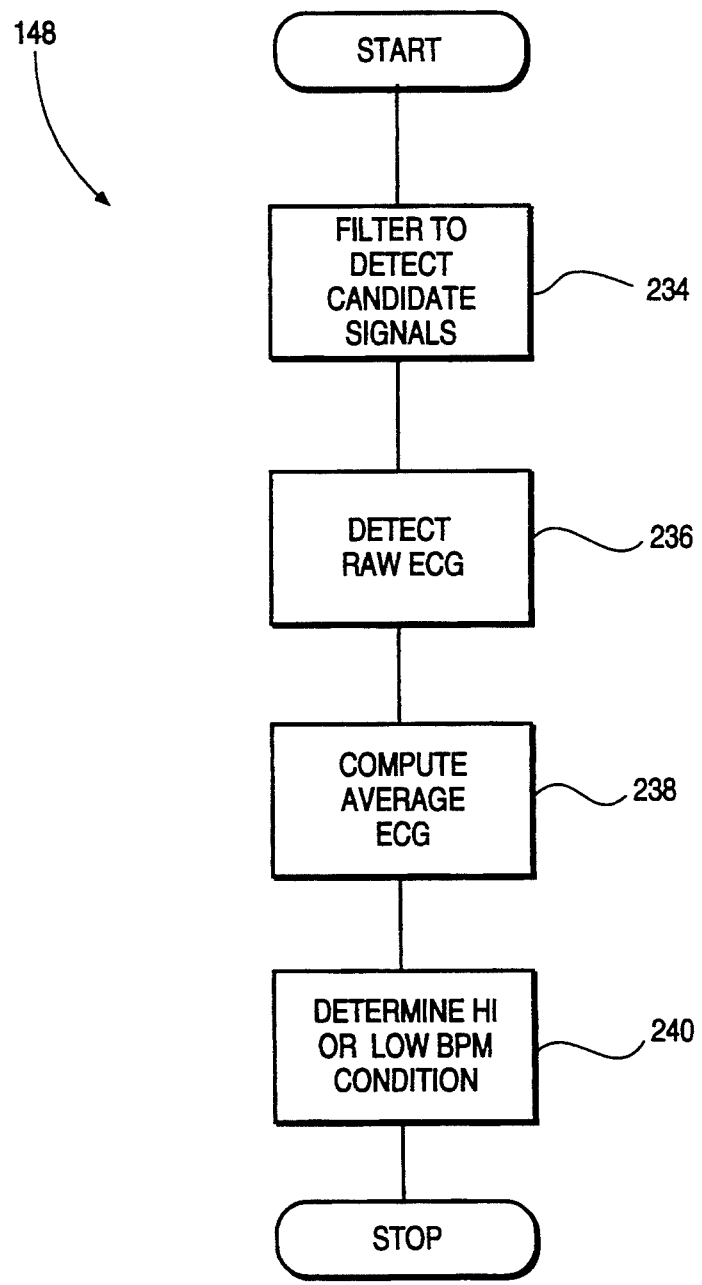
FIG. 16 is a logic flow chart illustrating the signal indication operation of the digital signal processor of the apparatus shown in FIG. 2 in accordance with a second technique.

Referring again to a block 236 of FIG. 16, additional logic may be included for detecting periodic signals in the user's raw ECG signal (i.e., the digitized biopotential signal that has not been autocorrelated). The raw ECG data yields a periodic signal that is a rough measure of heart rate (the "Raw ECG heart rate"). The Raw ECG heart rate is used by the arbitrator in selecting or rejecting candidate heart rate signals detected at block 234. At a block 238, the Raw ECG heart rate detected at block 238 is incorporated into a running average ("Average ECG heart rate") of the last 20 measured Raw ECG heart rate values. The Average ECG is also used by the arbitrator to select or reject the candidate signals detected at block 234, as explained below in greater detail.

At a block 240, digital signal processor 44 determines the existence of a "high" or "low" heart rate state. Generally, the Raw ECG heart rate measurements are more reliable in a "low" heart rate state. A low heart rate state exists if more than six two-second windows of A/D sample data have been taken since the user last removed his or her hands from the biopotential sensor 38 and both the Average ECG heart rate and each of the last six measured Raw ECG heart rate are below 85 beats per minute. A "high" heart rate state exists if more than six two-second windows of A/D sample data have been taken since the user last removed his hands from the biopotential sensor 38 and the Average ECG heart rate is above 95 and the last six measured Raw ECG heart rates are above 90. These determinations are made anew at each iteration of block 240.

A suitable technique for determining a Raw ECG heart rate is to scan the A/D sample data to locate the peak value over eight seconds' worth of data (here, 2000 samples). Once the eight-second peak is determined, the A/D sample data is then divided into 45 windows each containing 44 samples. Each window is scanned to locate all local peaks having a value greater than two-thirds of the eight-second peak. Digital signal processor 44 then calculates the intervals between each such peaks. Those intervals which correspond to a heart rate of between 50 and 200 beats per minute are considered valid intervals. The valid intervals are summed, and that sum is divided by the total number of valid intervals to arrive at Raw ECG heart rate. Other techniques may be used for deriving a Raw ECG heart rate.

7. Arbitration of Candidate Signals

Referring back to FIG. 10, the arbitration function of block 150 is discussed in greater detail. As explained above, the arbitration function selects or "arbitrates" a final heart rate signal when multiple candidate heart rate signals are generated at block 148. This selection is performed in accordance with certain predetermined criteria, including reasonableness criteria. These criteria can include the elapsed time which the user has been operating the exercise appliance 58, the value of the RPM signal (which indicates the effort being expended by the user), and the value of the previously selected candidate heart rates. If none of the candidate heart rate signals is acceptable, then the value of the previously selected arbitrated heart rate is used.

For example, in some cases candidate heart rates which are harmonics of previously selected heart rates are rejected. Thus, if a particular candidate heart rate is equal to the value of a previously selected heart rate divided or multiplied by a whole number, then that heart rate is rejected. Also if a particular candidate heart rate is equal to the RPM signal or a multiple thereof, then it is likely that the candidate heart rate is actually measuring the cycles of biopotential signals generated by the user's leg muscles as he pedals the bike at the rate indicated by the RPM signal. In such a case, that particular candidate heart rate is rejected. Similarly, if the previously selected heart rate is a very high heart rate, such as 150 beats per minute, and a candidate heart rate is a very low rate, such as 50 beats per minute, the candidate heart rate is rejected because it is unlikely that the user's heart rate would decrease from 150 beats per minute to 50 beats per minute in one sample cycle.

By way of another example, if a candidate heart rate is outside of a predetermined range (preferably fifty to two hundred BPM), it will be rejected because human beings typically have heart rates within known ranges. Thus, a candidate heart rate of ten beats per minute is rejected because it is too low. By way of another example, heart rate should increase with elapsed time and the value of the RPM signal. Thus, over time, a decreasing candidate heart rate is rejected in favor of an increasing candidate heart rate, particularly where the value of the RPM signal is steady or increasing.

By way of yet another example, in some exercise equipment, heart rate data is used to modulate the load resistance imposed on the user, and thereby maintaining the user's heart rate at a selected target level. Such a system is illustrated by U.S. patent application Ser. No. 07/881,918 filed May 12, 1992, the disclosure of which is hereby incorporated in its entirety. When practicing the present invention with such systems, the selected target rate can be used as one of the criteria for arbitrating the candidate rates. In particular, where the arbitrated value is sufficiently close (i.e., within five beats) to the target heart rate, the target heart rate itself can be displayed so that the user is not distracted by minor fluctuations in displayed heart rate.

Digital signal processor 44 performs the arbitration function by selecting one of these candidate heart rates. As explained above, the arbitration routine can use a number of selection criteria. However, it has been found through empirical testing that the following arbitration routine is particularly well-suited for use on stair climbers and treadmills. It is described with reference to the alternative candidate detection technique discussed in the preceding section, and is illustrated generally in the flow chart of FIG. 17. The various constant values and conditional logic statements described herein have been found effective with Life Fitness brand exercise equipment, but may require calibration and/or modification when practiced with other types of equipment.

This particular embodiment of the arbitration routine uses a two-tiered approach. Initially three first-tier selection criteria (shown in blocks 242-246) are used to select three finalists from the array of candidate signals generated at block 148 of FIG. 10 by the alternative detection techniques. The first-tier selection criteria are: (i) selecting the candidate ("HR1") with the largest pulse height; (ii) selecting the candidate ("HR2") with the strongest harmonics; and (iii) selecting the candidate ("HR3") which is closest to the current heart rate.

First First-Tier Selection Criteria

To select the candidate with the largest pulse height at block 242 digital signal processor 44 scans the candidate array to locate the candidate having the largest pulse height.

Second First-Tier Selection Criteria

Selecting the candidate with the strongest harmonics (HR2) is performed at block 244 in accordance with the following technique. Beginning with the first candidate in the candidate array, the array is scanned to locate any other candidates that are frequency harmonics (either one-half or one-third) of the first candidate. If harmonics are found, the pulse heights of the first candidate and its harmonics are added together to provide an aggregate harmonic pulse height. This aggregate harmonic pulse height is stored in a temporary list, along with the array index of the candidate and its one-half harmonic. This process is repeated for each successive candidate.

Once the list is completed, the digital signal processor 44 chooses between: (i) the candidate having the greatest aggregate harmonic; and (ii) that candidate's one-half harmonic. This selection is made in accordance with the following criteria:

(a) If the candidate falls outside the range of normal human heart rate (50-200 beats per minute), the candidate's one-half harmonic is selected as HR2. If the candidate's one-half harmonic falls outside the range of normal human heart rate (50-200 beats per minute), the candidate is selected as HR2.

(b) If both the candidate and its one-half harmonic fall within the normal heart rate range, then the current value of HR3 is compared to the larger (based on pulse height) of the candidate and its one-half harmonic. If the larger of the two is sufficiently close in beats per minute to the current value of HR3, it is selected as HR2. For purposes of the preceding sentence, the term "sufficiently close" means within six beats per minute of the current value of HR3, or within four beats per minute of the current value of HR3 divided by two. If the "sufficiently close" criteria is met by dividing the current value of HR3 by two, it is assumed that the selected value is actually the one-half harmonic of the "true" value, and accordingly, HR2 is set to twice the selected value.

(c) If the preceding test does not yield a valve for HR2, then the larger of the candidate and its one-half harmonic (based on pulse height) is compared to the current arbitrated heart rate in the same manner as described in the preceding paragraph with respect to HR3.

(d) If the preceding test does not yield an HR2, then the one-half harmonic is divided by the aggregate pulse height. If the resulting quotient is greater than 0.64, then it is assumed that one-half harmonic represents heart rate. Accordingly, the one-half harmonic is selected as HR2 unless either of the following conditions exists: (i) the one-half harmonic is less than eighty beats per minute and a high heart rate state exists (as determined at the block 240 of FIG. 16); or (ii): (x) the candidate heart rate is greater than 120 beats per minute, and (y) the Average ECG heart rate is greater than 103 beats per minute of the last six consecutive Raw ECG heart rate are each greater than 95.

(e) If the preceding test does not yield a HR2, and if the candidate heart rate is greater then 110 and a low heart rate state exists (as determined at the block 240 of FIG. 16), then the one-half harmonic is selected as HR2.

(f) If the candidate heart rate is greater than 150 and the Average ECG heart rate is less then 85, then the one-half harmonic is selected.

(g) if none of the foregoing tests yields a value for HR2, then the candidate is selected as the new HR2.

Third First-Tier Selection Criteria

Selecting the candidate which is closest to the current heart rate is performed at block 246 in accordance with the following technique. The candidate array is scanned to locate the candidate having the largest pulse height and a frequency that is approximately equal to the frequency of the currently selected heart rate or harmonic thereof. For purposes of the preceding sentence, the term "approximately equal" means that the candidate is within plus-or-minus: (i) eight beat beats of the currently arbitrated heart rate; (ii) six beats of the one-half harmonic of the currently arbitrated heart rate; or (iii) seven beats of the one-third harmonic of the currently arbitrated heart rate.

Selecting the candidate that is closest to the currently arbitrated heart rate tends to stabilize the system. There is, however, some risk that this routine may bias the system toward erroneous heart rate readings once those readings are accepted (such as in the case of a voltage spike or other aberration). To reduce this risk, the routine of block 246 is suppressed in certain circumstances. Specifically, in each iteration of block 246, the last-computed value of HR2 is stored in a three element array if it is sufficiently close to the last-computed value of HR1. For purposes of the preceding sentence, the term "sufficiently close" means that either: (i) HR1 and HR2 are within six beats of each other; or (ii) twice HR1 is within four beats of HR2. If HR2 is found to be sufficiently close only after doubling its value, then it is the doubled value that is placed into the three-element array. If each element of the three-element array is within six beats per minute of the its adjacent element, the closest-value routine of block 246 is suppressed, and the value of HR3 is simply set to the last-computed value of HR2 (instead of the candidate that is closest to the current arbitrated heart rate).

When the closest-value routine is suppressed as described above, it is sometimes the case that the value of HR2 differs by more than twenty beats from the last arbitrated heart rate. Because changes of such magnitude are unusual, digital signal processor 44 will conduct some additional processing before setting HR3 equal to HR2. Specifically, digital signal processor 44 compares both the current value of HR2 and current arbitrated heart rate with the average of the preceding ten values of HR2. It then selects as HR3 that one that is closest to the running average of HR2.

Figure 17:
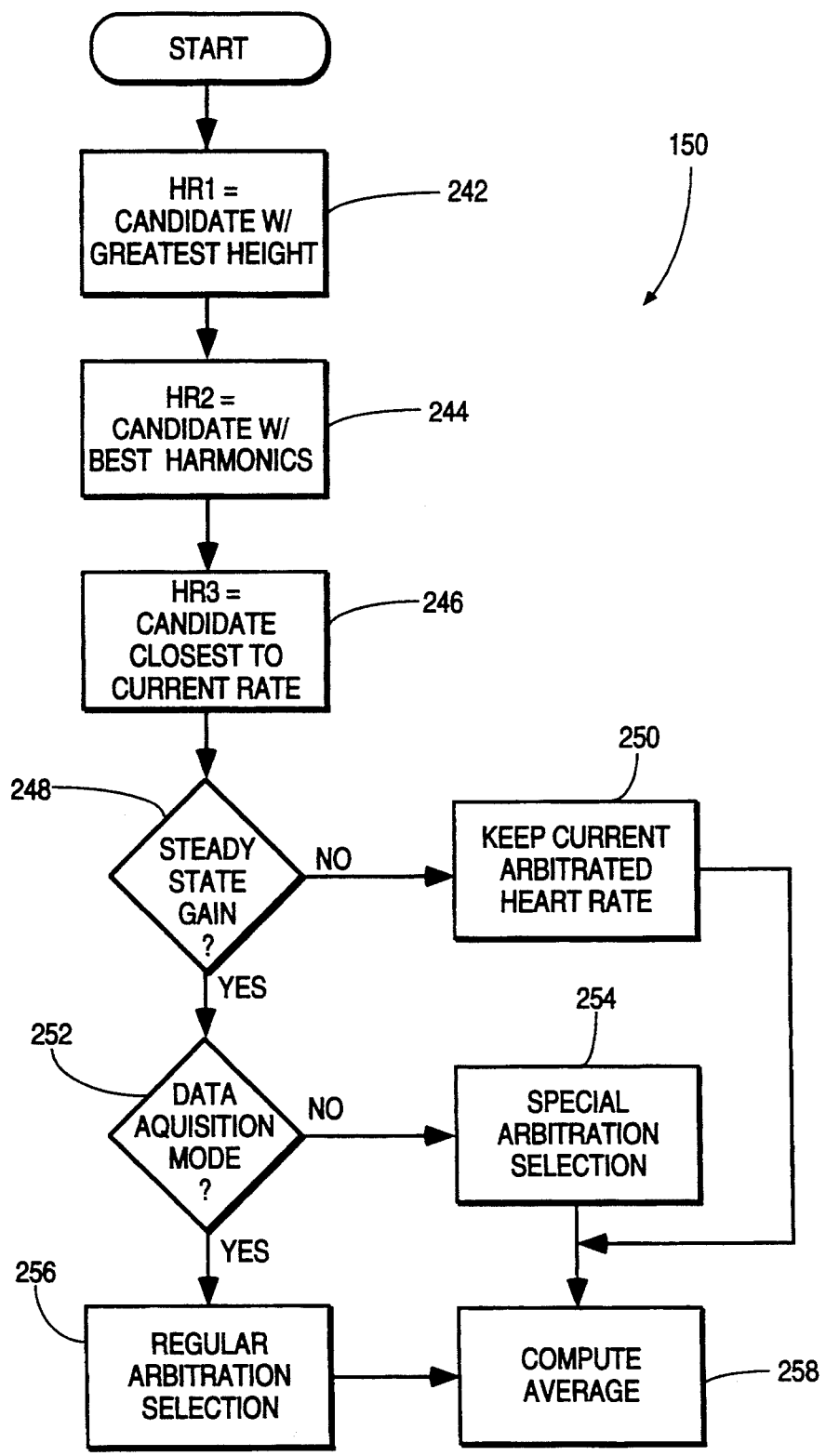
FIG. 17 is a logic flow chart illustrating the arbitration operation of the digital signal processor of the apparatus of FIG. 2.

Referring to FIG. 17, after the three finalists (HR1, HR2 and HR3) have been selected using the first-tier selection criteria in blocks 242-246, a set of second-tier criteria (shown in blocks 248-258) is used to make the ultimate selection from among the three finalists (or, in some cases, the Raw ECG values). It will be observed that the system is biased toward selecting HR2 as the arbitrated heart rate because it has been found to be a very reliable signal indication. It should also be noted that the second tier of arbitration is only necessary when the first tier yields more than one finalists. For example, if the invention is practiced only with the strongest harmonic routine of block 244, then the first tier of arbitration generates only HR2. In that case, HR2 would be the final arbitrated value. No second tier processing would be necessary.

The second tier process begins at block 248, where the digital signal processor 44 determines whether the amplifier gain command has reached a steady state. The amplifier gain command is discussed in more detail below. In general terms, however, a steady state gain command is associated with the user leaving his or her hands on the biopotential sensors 38 for sufficient time such that a clean biopotential signal is obtained. Thus, if gain has not reached a steady state, no arbitration occurs, and control moves to block 250 where the last-selected arbitrated heart rate is selected again as the new arbitrated heart rate. The logic of decision block 248 is qualified by the fact that gain is deemed to be "steady state" (for purposes of block 248 only) if HR2 equals HR3 and HR2 is sufficiently close to HR1.

If amplifier gain has reached a steady state, then control moves to the block 252 where digital signal processor 44 determines whether or not the heart rate monitor system is in data acquisition mode. For purposes of the preceding sentence, the term "data acquisition mode" means that heart rate data is being initially acquired either because the system has just been powered on; (ii) because the user has just replaced his or her hands on the biopotential sensors 38 after having had removed them for a period of time; or (iii) because the system has been reset because of poor signal quality as described below in connection with FIG. 18. In any event, data acquisition mode requires more stringent arbitration criteria, as provided by the special arbitration routine of block 254. If the system is not in data acquisition mode, control moves to the block 256 where the regular arbitration selection routine is performed.

After completion of blocks 250, 254 or 256, as the case may be, control moves to block 258 where the finally selected arbitrated heart rate is averaged with the four previously selected arbitrated heart rates. It is this average value which is provided to microprocessor 40 for display at block 152 of FIG. 10.

Figure 18:
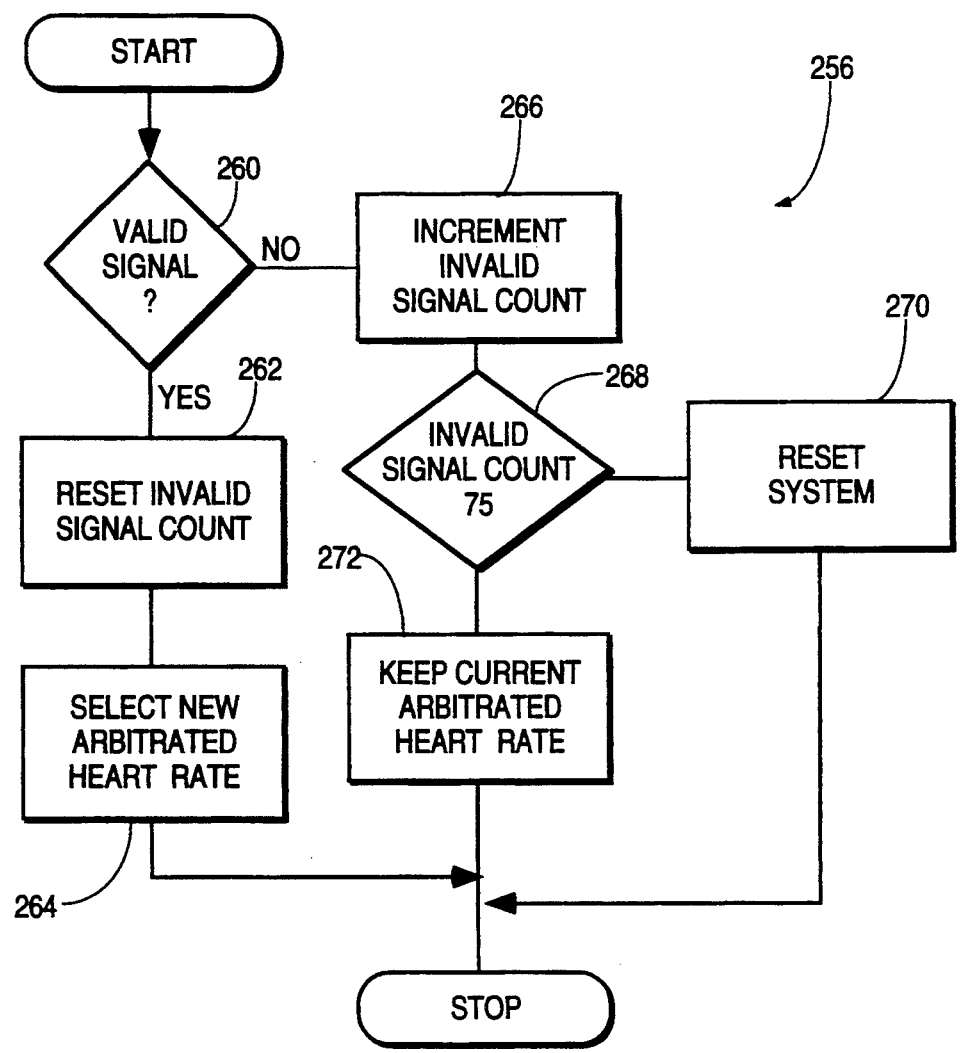
FIG. 18 is a logic flow chart illustrating in greater detail the arbitration operation shown in FIG. 17.

Referring to FIG. 18, the regular arbitration selection routine of block 256 in FIG. 17 is described in greater detail. Beginning at a block 260, digital signal processor 44 determines whether the current autocorrelation output represents a valid signal. This determination is made as follows: the average of the absolute values of the autocorrelation output are computed over the range of 38 beats per minute through 200 beats per minutes. Then, this average is multiplied by 7 to arrive at a first threshold value (THRH4); multiplied by 6 to arrive at a second threshold value (THRH5); and multiplied by 5.5 to arrive at a third threshold value (THRH6). The digital signal processor 44 then steps through the candidate array, successively examining each candidate's pulse height. If any candidate has a pulse height greater than THRH5, then the signal is considered valid. The signal will also be considered valid if any candidate has a pulse height greater than THRH6 and the candidate with the best harmonic (HR2) is sufficiently close in frequency to the candidate with the greatest pulse height (HR1). For purposes of the preceding sentence the term "sufficiently close" means that HR1 and HR2 are within six beats of each other, or twice HR1 is within four beats of HR2. It will be observed that the signal is considered valid if any candidate exceeds the lower threshold THRH6 so long as there is provided the additional assurance that HR1 and HR2 are sufficiently close. It will also be noted that the purpose of doubling HR1 in the foregoing calculations is to take into account situations where it is the one-half harmonic of the true signal.

If the signal is valid, control moves from the block 260 to block 262, where the invalid-signal-count (an integer discussed below in greater detail) is set to zero. Control then moves to block 264 where the final arbitrated heart rate is selected from among HR1, HR2, HR3, the current arbitrated heart rates and the Raw and Average ECG data. The selection process of block 264 is discussed below in greater detail.

If the autocorrelation signal is determined to be invalid, then control moves to a block 266 where the integer invalid-signal-count is incremented by one. Control then moves to a decision block 268 where the invalid-signal-count is compared to five. If the invalid signal count is greater than five, then control moves to block 270 where the system is reset as described below in greater detail. If the signal count is less than five, then control moves to block 272 where the current arbitrated heart rate is reselected to be the next arbitrated heart rate. The routine embodied by blocks 266 through 272 is based on the premise that the candidate signal should not be considered if the autocorrelation signal is considered invalid at block 260. Thus, the output of the arbitrator is simply the previously arbitrated heart rate. Moreover, if the signal is found to be invalid more than five times (as measured by the invalid-signal-count), then it is assumed that the signal is too noisy, and the system is reset at block 270. In resetting the system, the following occurs: the gain command (discussed below in greater detail) is reduced by eighty percent; the arbitrator returns a zero as the current arbitrated heart rate; the system suspends the measurement of autocorrelation, candidate signal detection and arbitration for four seconds; and system variables (including the arbitrated heart rate, average arbitrated heart rate, and Raw ECG values) are reinitialized.

It will be noted that when the user removes his or her hands from the biopotential sensor for more than one second, the system to is also reset at the block 132 of FIG. 9. When the user replaces his or her hands on the biopotential sensor 38, the system will begin to reacquire heart rate data. When the system reacquires heart rate, there is an eight-second delay while the system takes four two-second samples. During this delay, no heart rate is displayed. The absence of a display troubles some users. To reduce this delay in certain situations, historic arbitration and ECG data are preserved and reused if the user's hands are removed for less than sixteen seconds. By preserving this data, a heart rate can be displayed as soon as the user resumes contact with biopotential sensor 38. This approach is based on the premise that the user's heart rate does not vary substantially over a sixteen second period.

At block 264, the old arbitrated heart rate is reselected as the new arbitrated heart rate, unless one of the following conditional statements are executed:

(a) If HR2 equals zero and the current arbitrated heart rate is less than 100 and a low heart rate condition exists and Raw ECG heart rate is between 49 and 76 and the Average ECG heart rate is less than 80 and the average ECG heart rate is less than the current arbitrated heart rate minus fifteen, then select the Raw ECG heart rate as the new arbitrated heart rate.

(b) If a low heart rate condition exists and Raw ECG heart rate is between 49 and 76, and HR1 is less than 76 and HR2 equals zero and HR3 equals zero, then select HR1 as the new arbitrated heart rate.

(c) If Average ECG heart rate is less than 93 and Average ECG heart rate is greater than the current arbitrated heart rate plus fifteen, then select Average ECG heart rate as the new arbitrated heart rate.

(d) If: (i) HR3 is nonzero, and (ii) either twice HR1 is within four beats of HR3 or HR1 is within six beats of HR3, and (iii) HR3 equals HR2, then select HR3 as the new arbitrated heart rate.

(e) If HR3 is within eight beats of the current arbitrated heart rate, then select HR3 as the new arbitrated heart rate.

(f) If HR1 does not equal HR2, then perform the following conditional statements:

If HR1 is nonzero and HR1 equals HR3 select HR3 as the new arbitrated heart rate;

otherwise, if HR3 is nonzero and HR3 is within four of twice HR2, then select HR3 as the new arbitrated heart rate:

otherwise, if HR3 is nonzero and twice HR3 is within four of HR2, then select HR3 as the new arbitrated heart rate;

otherwise, if HR3 is nonzero and HR3 is within four of twice HR1, then select HR3 as the new arbitrated heart rate;

otherwise, if twice HR3 is within four of HR1, then select HR3 as the new arbitrated heart rate;

otherwise, if HR3 is within eight of the current arbitrated value, then select HR2 as the new arbitrated heart rate;

otherwise, if HR2 is within four of twice the current arbitrated value and HR2 divided by two is greater than or equal to 50, then select HR2 divided by two as the new arbitrated heart rate;

otherwise, if twice HR2 is within four of the current arbitrated value, then select twice HR2 as the new arbitrated heart rate;

otherwise, if HR1 is within eight of the current arbitrated value, then select HR1 as the new arbitrated heart rate;

otherwise, if HR1 is within four of twice the current arbitrated value and HR1 divided by two is greater than or equal to 50, then select HR1 divided by two as the new arbitrated heart rate;

otherwise, if twice HR2 is within four of the current arbitrated value, then select twice HR1 as the new arbitrated heart rate.

(g) If HR1 equals HR2 and both are within eight beats of the current arbitrated heart rate, then select HR1 as the new arbitrated heart rate.

(h) If HR1 equals HR2, and HR1 is within four beats of twice HR3, then perform the following conditional statements:

if a low heart rate condition exists and HR3 is greater than 50, then select HR3 as the new arbitrated heart rate;

otherwise, if Average ECG heart rate is greater than 105 and HR3 is less than or equal to 80 and the current arbitrated heart rate is less than or equal to 80, then select HR1 as the new arbitrated heart rate;

otherwise, if Average ECG heart rate is less than 70, then select HR3 as the new arbitrated heart rate.

(i) If HR1 equals HR2 and HR1 is not within eight beats of the current arbitrated heart rate and twice HR1 is within four beats of HR3, then select HR3 as the new arbitrated heart rate;

otherwise if: (a) the Average ECG heart rate is less than 80 and HR1 is less than 85 and the current arbitrated heart rate is greater than 100, or (b) the Average ECG heart rate is greater than 105 and HR1 is greater than 110 and the current arbitrated heart rate is less than 80, then select HR1 as the new arbitrated heart rate;

otherwise, if the current arbitrated heart rate is greater than 110 and HR1 is less than 80 and a low heart rate condition exists and Average ECG heart rate is less than 80, then select HR1 as the new arbitrated heart rate;

otherwise, if the Average ECG heart rate is greater than 105 and the current arbitrated heart rate is less than 80 and HR1 is greater than 110 and a high heart rate condition exists, then select HR1 as the new arbitrated heart rate.

Referring again to FIG. 17, the special arbitration routine of block 254 is similar to the regular arbitration routine of FIG. 19, except that it is biased toward selecting the current arbitrated heart rate. Notably, when the system is reset or initialized, the current arbitrated heart rate will be zero or other null value. Thus, the special arbitration routine tends to output a null value for heart rate unit a suitable signal is received.

Initially, the special arbitration routine determines whether a valid signal exists (as described above) or, if the system is being initialized, whether valid initial data exists. The determination of whether valid initial data exists is similar to the above-described determination of whether a valid signal exists, except that THRH4 is used in place of THRH5, and THRH5 is used in place of THRH6. Additional criteria are also used. First, if HR2 and HR3 are non-zero and equal, and if HR1 and HR2 are substantially close, then the initial data is considered valid. Second, if the current gain command is changed more than ten counts from the last gain command, then the initial data is considered invalid. Third, if the pulse height of the candidate having the best harmonic (HR2) has a pulse height that is below THPH, then the data is considered invalid. Fourth, if the number of candidates is less than three, the data is considered invalid. Fifth, if there are exactly three candidates, digital signal processor 44 computes the average of the highest and lowest frequencies. If this average is within one beat of the intermediate frequency, then the signal is considered valid.

If the valid signal or valid initial data condition is true, then the special arbitration selection routine selects an arbitrated heart rate by first determining whether an HR2 (best harmonics) candidate exists. If an HR2 candidate is not yet available, the current arbitrated heart rate is selected as the next arbitrated heart rate, unless one of the following conditions is true:

(a) If a valid waveform exists, then HR1 is selected as the new arbitrated heart rate; a valid waveform is deemed to exist if the last two HR1 values are each within ten beats per minute of the current HR1, or the last two HR2 values are each within ten beats per minute of the current HR1.
(b) otherwise if HR1 is less than 85 and a low heart rate condition exists, then HR1 is selected as the new arbitrated heart rate;
(c) otherswise if HR1 is less than 76 and HR1 is within ten of the Raw ECG heart rate and the Average ECG heart rate is less than 80 and a low heart rate condition exists, then the Raw ECG heart rate is selected as the new arbitrated heart rate.

If an HR2 (best harmonic) candidate is available, then the current arbitrated heart rate is selected as the next arbitrated heart rate, unless one of the following conditions is true:
(a) If HR2 equals HR3 and HR2 is sufficiently close to HR1, then HR2 is selected as the new arbitrated heart rate;
(b) otherwise if HR2 is within four of twice HR1, and HR2 is within four of twice the Average ECG heart rate, then HR1 is selected as the new arbitrated heart rate;
(c) otherwise if HR2 is within six of HR1 and: (i) HR2 is greater than or equal to 100 and the Average ECG heart rate is greater than 95, or (ii) HR2 is less than or equal to 90 and the Average ECG heart rate is less than 85, or (iii) HR2 is greater than 90 and HR2 is less than 110 and the Average ECG heart rate is less than 105 and the Average ECG heart rate is greater than 85, then HR2 is selected as the new arbitrated heart rate, but only if HR2 is below 180;
(d) otherwise if HR2 is within four of twice HR1 and the Average ECG heart rate is greater than 100, then HR2 is selected as the new arbitrated heart rate, but only if HR2 is below 180;
(e) otherwise if twice HR2 is within four of HR1 and the Average ECG heart rate is greater than 105, then HR1 is selected as the new arbitrated heart rate, but only if HR1 is below 100;
(f) otherwise if: (i) a low heart rate condition exists and the Average ECG heart rate is less than 80 and HR2 is less than 85, or (ii) a high heart rate condition exists and the Average ECG heart rate is greater than 105 and HR2 is greater than or equal to 110, then HR2 is selected as the new arbitrated heart rate, but only if it is below 195.

8. Alternative Technique for Filtering and Gain Control

As discussed above in connection with data acquisition, the user's biopotential signal is digitized by the A/D converter 42 and read by the microprocessor 40 at block 104 of FIG. 8. The microprocessor 40 then transmits the digitized biopotential signal to the digital signal processor 44, which filters the data at block 134 of FIG. 9. The digital signal processor 44 also adjusts the gain of the adjustable gain amplifier 94 to maintain the peak value of the A/D sample data within a predetermined range. This gain adjustment occurs at the block 142, as described above.

As explained above, the electrodes 48, 50 and 52 of biopotential sensor 38 are placed on the handlebars such as handlebars 68. In this manner, the user makes contact with the sensor 38 as a matter of course when using an exercise appliance, such as bicycle 58, stair climbing machine 200 or treadmill 202. With this arrangement, however, users are likely to move their hands on (or remove their hands from) the electrodes. This causes spikes and other noise which interferes with the users' biopotential signals.

To address this problem, alternative techniques for performing the filtering and gain-adjustment functions of blocks 134 and 142 are provided. With respect to the filtering function of block 132, prior to passing the signal through the digital filter, any A/D sample data which exhibits clipped voltage is set to baseline (or "zero") voltage. Clipping occurs when the sample voltage level is at the maximum or minimum voltage output of the variable gain amplifier 94. In this case, that maximum voltage is five volts. Any A/D sample data having a value of more than 4.9 or less than 0.1 is considered to be clipped, and is set to a baseline (or "zero") value. In this case, because voltage is scaled between 0.0 and 5.0, the baseline voltage is 2.5 volts. (In effect, values of 2.5 volts are "zero", and voltages values between 0.0 and 2.5 are "negative").

Clipping is particularly likely to arise when a user moves his or her hands on the biopotential electrodes 48, 50 and 52. This movement causes sudden voltage fluctuations. While the gain-adjustment function of block 142 theoretically could rescale the voltage to within the predetermined range, in practice the fluctuations caused by hand movement occur too quickly and intermittently. Clipping reduces the effectiveness of autocorrelation because it distorts wave shape. By setting clipped voltages to zero, clipped samples do not effect the results of the autocorrelation. They are in effect removed from statistical consideration. The number of clipped samples in each two-second window of A/D data is stored in a variable ("clip-count") for use by the sample gain control routine described below in greater detail.

It has been noted that the digital filtering in block 142 is effective in removing high frequency noise sometimes created when clipped values are set to zero.

With respect to the gain-adjustment function of block 142, the sudden voltage fluctuations which cause clipping may also lead to overcompensation of the gain, which in turn reduces the effectiveness of autocorrelation. Thus, it is advantageous to avoid overcompensating gain in response to sudden changes in such voltage. At the same time, it is important that the gain be set as high as possible for maximum sensitivity of biopotential sensor 38. To address these considerations, a more sophisticated gain-adjustment technique is employed. This technique is illustrated in FIG. 19.

As explained above in connection with block 142 of FIG. 10, every two seconds, digital signal processor 44 scans 500 A/D samples to determine the peak value over the two-second window. Digital signal processor 44 then sends a gain control command to biopotential sensor 38 via microprocessor 40 to adjust the amplification of adjustable gain amplifier 94. In this case, the gain command is an integer having a range of values from 0 (for minimum gain) to 99 (for maximum gain). Other values may be used. In this manner, the voltage generated as the output of the biopotential sensor 38 is maintained in the range of 0.0 to 5.0 volts, without significant clipping.

Referring to FIG. 19, the gain control routine begins at a block 274. The gain command is initially set at absolute minimum, here five percent of total magnitude.

Adjustments are then made to the gain on the basis of actual measured peak values. Once adjustments to the gain command are stabilized (a condition defined below in greater detail), subsequent gain adjustments are made on a basis of the average of the peak readings from the current and two preceding two-second windows. This averaging dampens fluctuations and gain and is described below in greater detail. Thus, at block 274 if gain is stable, and clip-count (defined above) is less than ten, then the peak value is included in the running average. Control then moves to a decision block 276 where control branches to block 278 if gain is stable, and block 280 if gain is not yet stable. At block 280 the gain is adjusted by setting the gain command equal to the current gain command multiplied by $A_1$ where $A_1$ is defined as optimal peak divided by current peak. In this case, the optimal peak is 4.625 volts. It will observed that the foregoing adjustment is made on the basis of the last-read peak and not on the basis of the average peak. The average values of the preceding two peaks are used only where gain is stable as discussed below.

It should also be noted that the adjustment is based on peaks as opposed to pulse height because peaks measure that portion of the wave from above the "zero" or baseline value (in this case 2.5 volts), the quantities in the foregoing equation (as well as in $A_2$ specified below) should be scaled by subtracting 2.5 volts. Thus, if the actual peak is 4.9 volts, and the optimum peak value is 4.265 volts, the value of $A_1$ is $(4.625-2.5) \div (4.9-2.5)$.

If gain is stable, control moves to the block 278, where digital signal processor 44 determines whether adjustment conditions exist. While these adjustment conditions may vary from implementation to implementation, in the present embodiment, adjustment will occur if the following are true: (i) the average of the current peak and the preceding two peaks is outside the optimum range, or the most recently read peak is below the optimum range; and (ii) the clip-count equals zero or the clip count is less than five and the average peak value is below the optimum range. If the adjustment conditions exist, control moves to block 282 where gain is adjusted by setting the gain control command equal to the current gain control command multiplied by $A_2$, where $A_2$ equals optimal peak divided by average peak.

If the adjustment conditions do not exist at block 278, control continues to block 283. At block 283 digital signal processor 44 sets a gain-stable flag to true if the last three gain settings are within ten percent of the current gain setting. The gain stable flag is used at blocks 274 and 276 to determine if gain is in a stable state. Once the gain stable flag is set true it remains true until the system is reinitialized either by the user removing his hands from the biopotential sensor 38 or by program at block 270 of FIG. 18.

Control then continues to a block 284 where the dynamic minimum is adjusted to eighty percent of the current gain. Dynamic minimum is a variable which is employed when gain is adjusted at the above-described blocks 280 and 282. Regardless of the value of $A_1$ and $A_2$, gain is not set below the dynamic minimum. This prevents the gain from being set too low, which may lead to an undesirable decrease in sensitivity of the system.

Control then moves to a block 286, where gain is decreased by one in the event that an excessive amount of clipping is experienced. To determine whether an excessive amount of clipping is experienced, a special variable ("clip-num") is initialized at zero and is incremented once during each iteration of the gain control routine in which the two-second clip count exceeds the critical threshold (in this case, fifteen). Once the clipnum variable is greater than a predetermined constant (in this case, three) the gain is automatically decremented by one regardless of its present value and without regard to the dynamic minimum. Gain is not, however, reduced below the absolute minimum (here, five percent of total magnitude). Whenever a gain is decremented by one, the clip-num variable is reset to zero.

Control then moves to block 288. If the clip count is zero, then the variable clip is also set to zero. The clip count variable is then set to zero. The gain determined as a result of the gain control routine is recorded in memory so that it may be used at the above described block 283 to determine if gain is stabilized.

We claim:

1. An apparatus for measuring the heart rate of a person during exercise, comprising:
   a biopotential sensor adapted for contact with the user and capable of generating an input signal that includes the biopotential signal produced by the user's heart;
   an autocorrelator responsive to the input signal, the autocorrelator generating an autocorrelation signal of the input signal;
   signal processing means for detecting the indications of periodic signals in the autocorrelation signal and generating candidate signals corresponding to each of the detected indications, the indications being pulses in the autocorrelation signal which meet all of a predetermined plurality of filtering criteria;
   arbitration means for selecting that one of the candidate signals which is most likely a true heart rate in accordance with a plurality of predetermined arbitration criteria; and
   memory means for storing a current heart rate value, the memory means being responsive to the arbitration means for setting the current heart rate value to the value of the candidate signal selected by the arbitration means.

2. The apparatus of claim 1, wherein the predetermined filtering criteria include selecting those pulses having:
   (a) a pulse height greater than a predetermined threshold value,
   (b) a pulse width that is within a predetermined range, and
   (c) a pulse shape that has a local peak between, and in close proximity to, two local minimums.

3. The apparatus of claim 2, wherein the predetermined filtering criteria further include selecting those pulses which are substantially vertically symmetrical.

4. The apparatus of claim 1 further comprising raw ECG means for detecting a raw ECG signal corresponding to heart rate in the input signal, wherein at least one of the predetermined arbitration criteria is the value of the signal.

5. The apparatus of claim 1 wherein the biopotential sensor includes an amplifier that is adjustable in response to a variable gain control signal, and the signal processing means includes means for generating the gain control signal, and wherein the arbitration means selects one of the candidates signals only if the gain control signal is in a steady state.

6. The apparatus of claim 1 wherein the arbitration criteria include selecting the candidate signal with the largest pulse height, selecting the candidate with the strongest harmonics, and selecting the candidate which is closest to the current heart rate value.

7. A method for measuring the heart rate of a person during exercise, comprising:
generating an input signal that includes the biopotential signal produced by the user's heart;
generating an output signal that is the autocorrelation of the input signal;
detecting the indications of periodic signals in the autocorrelation output signal, said detection being accomplished by selecting as candidate signals those detected indications which meet all of a plurality of predetermined filtering criteria;
selecting one of the candidate signals as the current heart rate in accordance with a plurality of predetermined arbitration criteria; and
maintaining in memory the value of the current heart rate.

8. The method of claim 7, wherein the predetermined filtering criteria include selecting those pulses having:
(a) a pulse height greater than a predetermined threshold value,
(b) a pulse width that is within a predetermined range, and
(c) a pulse shape that has a local peak between, and in close proximity to, two local minimums.

9. The method of claim 8, wherein the predetermined filtering criteria further include selecting those pulses which are substantially vertically symmetrical.

10. The method claim 7 further comprising the steps of detecting a raw ECG signal from the input signal, and using the value of the raw ECG signal as one of the predetermined arbitration criteria.

11. The method of claim 7 wherein the step of selecting one of the candidate signals is performed in accordance with a plurality of first-tier arbitration criteria, which include
(a) selecting as the largest candidate that candidate with the largest pulse height,
(b) selecting as the strongest candidate that candidate with the strongest harmonics, and
(c) selecting as the closest candidate that candidate which is closest to the current heart rate value.

12. The method of claim 11 wherein the step of selecting one of the candidate signals includes the step of selecting one of the largest, strongest and closest candidate signals in accordance with second-tier arbitration criteria.

13. The method of claim 12 wherein the second-tier arbitration criteria include a first and second sets of second-tier arbitration criteria, wherein the step of selecting one of the largest, strongest and closest candidate signals is initially performed in accordance with the first set of second-tier arbitration criteria, and then, after a predetermined time period, is performed in accordance with the second set of second-tier arbitration criteria.

14. The method of claim 7, further comprising the steps of
generating a variable gain control signal in accordance with the amplitude of the input signal;
amplifying the input signal in accordance with a gain control signal to maintain the amplitude of the input signal within a predetermined range; and
determining if the gain control signal is at a steady state;
wherein the step of selecting one of the candidate signals in accordance with predetermined arbitration criteria is performed only when the gain control signal is at a steady state.

15. A method for measuring the heart rate of a person during exercise, comprising:
generating an input signal that includes the biopotential signal produced by the user's heart;
determining whether the input signal has exceeded predetermined positive and negative voltage limits, and setting the input signal to a null value when such limits are exceeded;
generating an output signal that is the autocorrelation of the input signal;
detecting the indications of periodic signals in the autocorrelation output signal, and selecting as candidate signals those indications which meet predetermined filtering criteria;
selecting one of the candidate signals in accordance with a plurality of predetermined arbitration criteria.

16. The method of claim 15 further comprising the steps of:
detecting the peak amplitude in the input signal over a predetermined time span;
generating a variable gain control signal in accordance with the detected peak amplitude;
amplifying the input signal in accordance with the gain control signal.

17. The method of claim 16 further comprising the step of:
counting the times the number of times the input signal is set to a null value during a predetermined time period;
decrementing the variable gain control signal by a predetermined amount if the count exceeds a predetermined threshold for a predetermined number of time periods.

18. The method of claim 15 wherein if the variable gain control is in a steady state, then the step of generating the variable gain control signal is performed in accordance with the average of the most-recently detected peak amplitude and at least one previously detected peak amplitude.

* * * * *